US005756470A

United States Patent [19]

Yumibe et al.

[11] Patent Number: 5,756,470
[45] Date of Patent: May 26, 1998

[54] SUGAR-SUBSTITUTED 2-AZETIDINONES USEFUL AS HYPOCHOLESTEROLEMIC AGENTS

[75] Inventors: Nathan P. Yumibe. Bergenfield; Kevin B. Alton. Cedar Knolls; Margaret Van Heek. Scotch Plains; Harry R. Davis. Berkeley Heights. all of N.J.; Wayne D. Vaccaro. Yardley, Pa.

[73] Assignee: Schering Corporation. Kenilworth, N.J.

[21] Appl. No.: 741,179

[22] Filed: Oct. 29, 1996

[51] Int. Cl.$^6$ .................. A61K 31/70; C07H 15/00
[52] U.S. Cl. .................. 514/25; 536/17.4; 536/18.1
[58] Field of Search .................. 536/4.1, 17.2, 536/18.1, 17.4; 514/25

[56] References Cited

U.S. PATENT DOCUMENTS

| 4,602,003 | 7/1986 | Malinow | 514/26 |
| 4,602,005 | 7/1986 | Malinow | 514/26 |

FOREIGN PATENT DOCUMENTS

| 199630 | 10/1986 | European Pat. Off. |
| 337549 | 10/1989 | European Pat. Off. |
| WO93/02048 | 2/1993 | WIPO |
| WO93/07167 | 4/1993 | WIPO |
| WO93/11150 | 6/1993 | WIPO |
| WO94/00480 | 1/1994 | WIPO |
| WO94/17038 | 8/1994 | WIPO |
| WO95/08532 | 3/1995 | WIPO |
| WO95/18143 | 10/1995 | WIPO |
| WO95/26334 | 10/1995 | WIPO |
| WO96/16037 | 5/1996 | WIPO |

OTHER PUBLICATIONS

Witzum, *Circulation*, 80, 5 (1989), pp. 1101–1114.
Illingworth, *Drugs*, 36(Supp. 3) (1988), pp. 63–71.
*Atherosclerosis*, 115 (1995), pp. 45–63.
Sybertz et al. "SCH 48461, a novel inhibitor of cholesterol absorption," *Athersclerosis X*, ed. Woodford et al (Elsevier Science B.V., 1995), pp. 311–315.

*Primary Examiner*—Elli Peselev
*Attorney, Agent, or Firm*—Anita W. Magatti

[57] ABSTRACT

Hypocholesterolemic sugar-substituted 2-azetidinones are disclosed, as well as a method of lowering cholesterol by administering said compounds, pharmaceutical compositions containing them, and the combination of a sugar-substituted 2-azetidinone cholesterol-lowering agent and a cholesterol biosynthesis inhibitor for the treatment and prevention of atherosclerosis.

20 Claims, No Drawings

SUGAR-SUBSTITUTED 2-AZETIDINONES USEFUL AS HYPOCHOLESTEROLEMIC AGENTS

BACKGROUND OF THE INVENTION

The present invention relates to sugar-substituted 2-azetidinones useful as hypocholesterolemic agents in the treatment and prevention of atherosclerosis, and to the combination of a sugar-substituted 2-azetidinone of this invention and a cholesterol biosynthesis inhibitor for the treatment and prevention of atherosclerosis.

Atherosclerotic coronary heart disease represents the major cause for death and cardiovascular morbidity in the western world. Risk factors for atherosclerotic coronary heart disease include hypertension, diabetes mellitus, family history, male gender, cigarette smoke and serum cholesterol. A total cholesterol level in excess of 225–250 mg/dl is associated with significant elevation of risk.

Cholesteryl esters are a major component of atherosclerotic lesions and the major storage form of cholesterol in arterial wall cells. Formation of cholesteryl esters is also a key step in the intestinal absorption of dietary cholesterol. In addition to regulation of dietary cholesterol, the regulation of whole-body cholesterol homeostasis in humans and animals involves modulation of cholesterol biosynthesis, bile acid biosynthesis, and the catabolism of the cholesterol-containing plasma lipoproteins. The liver is the major organ responsible for cholesterol biosynthesis and catabolism and, for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When cholesterol absorption in the intestines is reduced, by whatever means, less cholesterol is delivered to the liver. The consequence of this action is a decreased hepatic lipoprotein (VLDL) production and an increase in the hepatic clearance of plasma cholesterol, mostly as LDL. Thus, the net effect of an inhibition of intestinal cholesterol absorption is a decrease in plasma cholesterol levels.

Several 2-azetidinone compounds have been reported as being useful in lowering cholesterol and/or in inhibiting the formation of cholesterol-containing lesions in mammalian arterial walls: WO 93/02048 describes 2-azetidinone compounds wherein the 3-position substituent is arylalkylene, arylalkenylene or arylalkylene wherein the alkylene, alkenylene or alkyleneportion is interrupted by a hetero atom, phenylene or cycloalkylene; WO 94/17038 describes 2-azetidinone compounds wherein the 3-position substituent is an arylalkylspirocyclic group; WO 95/08532 describes 2-azetidinone compounds wherein the 3-position substituent is an arylalkylene group substituted in the alkylene portion by a hydroxy group; PCT/US95/03196, filed Mar. 22, 1995, describes compounds wherein the 3-position substituent is an aryl(oxo or thio)alkylene group substituted in the alkylene portion by a hydroxy group; and U.S. Ser. No. 08/463, 619, filed Jun. 5, 1995, describes the preparation of compounds wherein the 3-position substituent is an arylalkylene group substituted in the alkylene portion by a hydroxy group, and wherein the alkylene group is attached the the azetidinone ring by a —S(O)$_{0-2}$— group. The cited patent applications are incorporated herein by reference.

Also, European Patent 199,630 and European Patent Application 337,549 disclose elastase inhibitory substituted azetidinones said to be useful in treating inflammatory conditions resulting in tissue destruction which are associated with various disease states, e.g. atherosclerosis.

Other known hypocholesterolemics include plant extracts such as sapogenins, in particular tigogenin and diosgenin. Glycoside derivatives of tigogenin and/or diosgenin are disclosed in PCT International publications WO 94/00480 and WO 95/18143.

The inhibition of cholesterol biosynthesis by 3-hydroxy-3-methylglutaryl coenzyme A reductase (EC1.1.1.34) inhibitors has been shown to be an effective way to reduce plasma cholesterol (Witzum, *Circulation*, 80, 5 (1989), p. 1101–1114) and reduce atherosclerosis. Combination therapy of an HMG CoA reductase inhibitor and a bile acid sequestrant has been demonstrated to be more effective in human hyperlipidemic patients than either agent in monotherapy (Illingworth, *Drugs*, 36 (Suppl. 3) (1988), p. 63–71).

SUMMARY OF THE INVENTION

The present invention relates to sugar-substituted 2-azetidinones, especially to glucose-derived conjugates of cholesterol-lowering 2-azetidinones having an aryl or substituted aryl group as a substituent at the 1-position and having a hydroxy-substituted phenyl group, especially a 4-hydroxyphenyl group, at the 4-position.

Compounds of the present invention are represented by the formula I

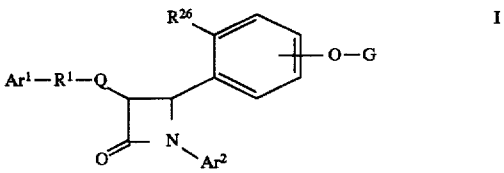

or a pharmaceutically acceptable salt thereof, wherein $R^{26}$ is H or $OG^1$;

G and $G^1$ are independently selected from the group consisting of

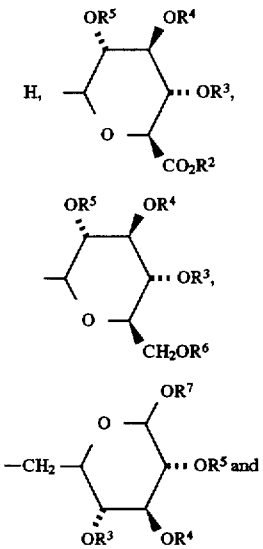

—(C$_2$–C$_6$)alkenylene-; and

—(CH$_2$)$_{f-V-(CH2)_g}$—, wherein V is C$_3$–C$_6$ cycloalkylene, f is 1–5 and g is 0–5, provided that the sum of f and g is 1–6;

R$^{12}$ is $$-CH-,\ -C(C_1\text{-}C_6\ \text{alkyl})-,\ -CF-,\ -C(OH)-,$$

$$-C(C_6H_4-R^{23})-,\ -N-,\ \text{or}\ -^+NO^-;$$

provided that when R$^{26}$ is H or OH, G is not H;

R, R$^a$ and R$^b$ are independently selected from the group consisting of H, —OH, halogeno, —NH$_2$, azido, (C$_1$–C$_6$)alkoxy(C$_1$–C$_6$)alkoxy or —W—R$^{30}$;

W is independently selected from the group consisting of —NH—C(O)—, —O—C(O)—, —O—C(O)—N(R$^{31}$)—, —NH—C(O)—N(R$^{31}$)— and —O—C(S)—N(R$^{31}$)—;

R$^2$ and R$^6$ are independently selected from the group consisting of H, (C$_1$–C$_6$)alkyl, aryl and aryl(C$_1$–C$_6$) alkyl;

R$^3$, R$^4$, R$^5$, R$^7$, R$^{3a}$ and R$^{4a}$ are independently selected from the group consisting of H, (C$_1$–C$_6$)alkyl, aryl (C$_1$–C$_6$)alkyl, —C(O)(C$_1$–C$_6$)alkyl and —C(O)aryl;

R$^{30}$ is independently selected form the group consisting of R$^{32}$-substituted T, R$^{32}$-substituted-T-(C$_1$–C$_6$)alkyl, R$^{32}$-substituted-(C$_2$–C$_4$)alkenyl, R$^{32}$-substituted-(C$_1$–C$_6$)alkyl, R$^{32}$-substituted-(C$_3$–C7)cycloalkyl and R$^{32}$-substituted-(C$_3$–C7)cycloalkyl(C$_1$–C$_6$)alkyl;

R$^{31}$ is independently selected from the group consisting of H and (C$_1$–C$_4$)alkyl;

T is independently selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

R$^{32}$ is independently selected from 1–3 substituents independently selected from the group consisting of halogeno, (C$_1$–C$_4$)alkyl, —OH, phenoxy, —CF$_3$, —NO$_2$, (C$_1$–C$_4$)alkoxy, methylenedioxy, oxo, (C$_1$–C$_4$) alkylsulfanyl, (C$_1$–C$_4$)alkylsulfinyl, (C$_1$–C$_4$) alkylsulfonyl, —N(CH$_3$)$_2$, —C(O)—NH(C$_1$–C$_4$)alkyl, —C(O)—N((C$_1$–C$_4$)alkyl)$_2$, —C(O)—(C$_1$–C$_4$)alkyl, —C(O)—(C$_1$–C$_4$)alkoxy and pyrrolidinylcarbonyl; or R$^{32}$ is a covalent bond and R$^{31}$, the nitrogen to which it is attached and R$^{32}$ form a pyrrolidinyl, piperidinyl, N-methyl-piperazinyl, indolinyl or morpholinyl group, or a (C$_1$–C$_4$)alkoxycarbonyl-substituted pyrrolidinyl, piperidinyl, N-methylpiperazinyl, indolinyl or morpholinyl group;

Ar$^1$ is aryl or R$^{10}$-substituted aryl;

Ar$^2$ is aryl or R$^{11}$-substituted aryl;

Q is a bond or, with the 3-position ring carbon of the azetidinone, forms the spiro group $$\diagdown R^{12}\text{-}(R^{13})_a$$
$$(R^{14})_b\text{-}\diagup\ ;$$

and

R$^1$ is selected from the group consisting of

—(CH$_2$)q—, wherein q is 2–6, provided that when Q forms a spiro ring, q can also be zero or 1;

—(CH$_2$)$_e$—E—(CH$_2$)$_r$—, wherein E is —O—, —C(O)—, phenylene, —NR$^{22}$— or —S(O)$_{0-2}$—, e is 0–5 and r is 0–5, provided that the sum of e and r is 1–6;

R$^{13}$ and R$^{14}$ are independently selected from the group consisting of —CH$_2$—, —CH(C$_1$–C$_6$ alkyl)-, —C(di-(C$_1$–C$_6$) alkyl), —CH=CH— and —C(C$_1$–C$_6$ alkyl)=CH—; or R$^{12}$ together with an adjacent R$^{13}$, or R$^{12}$ together with an adjacent R$^{14}$, form a —CH=CH— or a —CH=C(C$_1$–C$_6$ alkyl)- group;

a and b are independently 0, 1, 2 or 3, provided both are not zero; provided that when R$^{13}$ is —CH=CH— or —C(C$_1$–C$_6$ alkyl)=CH—, a is 1; provided that when R$^{14}$ is —CH=CH— or —C(C$_1$–C$_6$ alkyl)=CH—, b is 1; provided that when a is 2 or 3, the R$^{13}$'s can be the same or different; and provided that when b is 2 or 3, the R$^{14}$'s can be the same or different;

and when Q is a bond, R$^1$ also can be:

$$-M-Y_d-\underset{R^{16}}{\overset{R^{15}}{C}}-Z_h-,\ -X_m-(C)_s-Y_n-(C)_t-Z_p-\ \text{or}$$

$$-X_j-(C)_v-Y_k-S(O)_{0-2}-;$$

M is —O—, —S—, —S(O)— or —S(O)$_2$—;

X, Y and Z are independently selected from the group consisting of —CH$_2$—, —CH(C$_1$–C$_6$)alkyl- and —C(di-(C$_1$–C$_6$)alkyl);

R$^{10}$ and R$^{11}$ are independently selected from the group consisting of 1–3 substituents independently selected from the group consisting of (C$_1$–C$_6$)alkyl, —OR$^{19}$, —O(CO)R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^{20}$R$^{25}$, —NR$^1$ $^9$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_2$)$_{1-10}$—COOR$^{19}$, —O(CH$_2$)$_{1-10}$CONR$^{19}$R$^{20}$, —(C$_1$–C$_6$ alkylene)—COOR$^{19}$, —CH=CH—COOR$^{19}$, —CF$_3$, —CN, —NO$_2$ and halogen;

R$^{15}$ and R$^{17}$ are independently selected from the group consisting of —OR$^{19}$, —O(CO)R$^{19}$, —O(CO)OR$^{21}$ and —O(CO)NR$^{19}$R$^{20}$; R$^{16}$ and R$^{18}$ are independently selected from the group consisting of H, (C$_1$–C$_6$)alkyl and aryl; or R$^{15}$ and R$^{16}$ together are =O, or R$^{17}$ and R$^{18}$ together are =O;

d is 1, 2 or 3;

h is 0, 1,2,3 or 4;

s is 0 or 1; t is 0 or 1; m, n and p are independently 0–4; provided that at least one of s and t is 1, and the sum of m, n, p, s and t is 1–6; provided that when p is 0 and t is 1, the sum of m, s and n is 1–5; and provided that when p is 0 and s is 1, the sum of m, t and n is 1–5;

v is 0 or 1;

j and k are independently 1–5, provided that the sum of j, k and v is 1–5;

and when Q is a bond and $R^1$ is

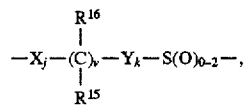

$Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, $(C_1–C_6)$alkyl, aryl and aryl-substituted $(C_1–C_6)$alkyl;

$R^{21}$ is $(C_1–C_6)$alkyl, aryl or $R^{24}$-substituted aryl;

$R^{22}$ is H, $(C_1–C_6)$alkyl, aryl $(C_1–C_6)$alkyl, —C(O)$R^{19}$ or —COO$R^{19}$;

$R^{23}$ and $R^{24}$ are independently 1–3 groups independently selected from the group consisting of H, $(C_1–C_6)$alkyl, $(C_1–C_6)$alkoxy, —COOH, $NO_2$, —$NR^{19}R^{20}$, —OH and halogeno; and $R^{25}$ is H, —OH or $(C_1–C_6)$alkoxy.

$Ar^2$ is preferably phenyl or $R^{11}$-phenyl, especially (4-$R^{11}$)-substituted phenyl. Preferred definitions of $R^{11}$ are lower alkoxy, especially methoxy, and halogeno, especially fluoro.

$Ar^1$ is preferably phenyl or $R^{10}$-substituted phenyl, especially (4-$R^{10}$)-substituted phenyl. A preferred definition of $R^{10}$ is halogeno, especially fluoro.

There are several preferred definitions for the —$R^1$—Q— combination of variables:

Q is a bond and $R^1$ is lower alkylene, preferably propylene;

Q is a spiro group as defined above, wherein preferably $R^{13}$ and $R^{14}$ are each ethylene and $R^{12}$ is

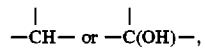

and $R^1$ is —$(CH_2)_q$ wherein q is 0–6;

Q is a bond and $R^1$ is

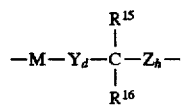

wherein the variables are chosen such that $R^1$ is —O—$CH_2$—CH(OH)—;

Q is a bond and $R^1$ is

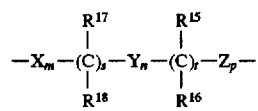

wherein the variables are chosen such that $R^1$ is —CH(OH)—$(CH_2)_2$—; and

Q is a bond and $R^1$ is

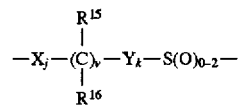

wherein the variables are chosen such that $R^1$ is —CH(OH)—$CH_2$—$S(O)_{0-2}$—.

A preferred compound of formula I, therefore, is one wherein G and $G^1$ are as defined above and in which the remaining variables have the following definitions:

$Ar^1$ is phenyl or $R^{10}$-substituted phenyl, wherein $R^{10}$ is halogeno;

$Ar^2$ is phenyl or $R^{11}$-phenyl, wherein $R^{11}$ is 1 to 3 substituents independently selected from the group consisting of $C_1–C_6$ alkoxy and halogeno;

Q is a bond and $R^1$ is lower alkylene; Q, with the 3-position ring carbon of the azetidinone, forms the group

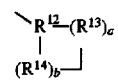

wherein preferably $R^{13}$ and $R^{14}$ are each ethylene and a and b are each 1, and wherein $R^{12}$ is

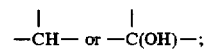

Q is a bond and $R^1$ is —O—$CH_2$—CH(OH)—; Q is a bond and $R^1$ is —CH(OH)—$(CH_2)_2$—; or Q is a bond and $R^1$ is —CH(OH)—$CH_2$—$S(O)_{0-2}$—.

Preferred variables for G and $G^1$ groups of the formula

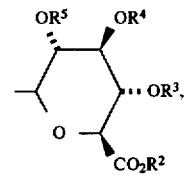

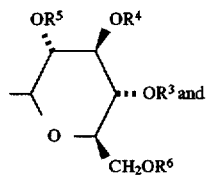

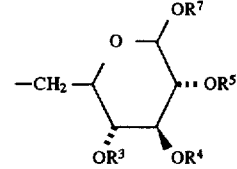

are as follows:

$R^2$, $R^3$, $R^4$, $R^5$, $R^6$ and $R^7$ are independently selected from the group consisting of H, $(C_1–C_6)$alkyl, benzyl and acetyl.

Preferred variables for group G or G¹ of the formula

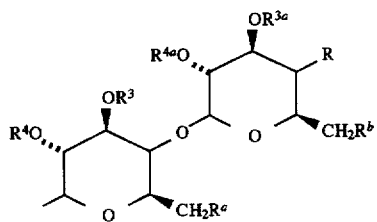

are as follows:

$R^3$, $R^{3a}$, $R^4$ and $R^{4a}$ are selected from the group consisting of H, $(C_1-C_6)$alkyl, benzyl and acetyl;

R, $R^a$ and $R^b$ are independently selected from the group consisting of H, —OH, halogeno, —$NH_2$, azido, $(C_1-C_6)$alkoxy$(C_1-C_6)$alkoxy and —W—$R^{30}$, wherein W is —O—C(O)— or —O—C(O)—$NR^{31}$—, $R^{31}$ is H and $R^{30}$ is $(C_1-C_6)$alkyl, —C(O)—$(C_1-C_4)$alkoxy-$(C_1-C_6)$alkyl, T, T—$(C_1-C_6)$alkyl, or T or T—$(C_1-C_6)$alkyl wherein T is substituted by one or two halogeno or $(C_1-C_6)$alkyl groups.

Preferred $R^{30}$ substituents are 2-fluorophenyl, 2,4-difluorophenyl, 2,6-dichlorophenyl, 2-methylphenyl, 2-thienylmethyl, 2-methoxycarbonylethyl, thiazol-2-ylmethyl, 2-furyl, 2-methoxycarbonylbutyl and phenyl. Preferred combinations of R, $R^a$ and $R^b$ are as follows: 1) R, $R^a$ and $R^b$ are independently —OH or —O—C(O)—NH—$R^{30}$, especially wherein $R^a$ is —OH and R and $R^b$ are —O—C(O)—NH—$R^{30}$ and $R^{30}$ is selected from the preferred substituents identified above, or wherein R and $R^a$ are —OH and $R^b$ is —O—C(O)—NH—$R^{30}$ wherein $R^{30}$ is 2-fluorophenyl, 2,4-difluorophenyl, 2,6-dichlorophenyl; 2) $R^a$ is —OH, halogeno, azido or $(C_1-C_6)$alkoxy$(C_1-C_6)$alkoxy, $R^b$ is H, halogeno, azido or $(C_1-C_6)$alkoxy$(C_1-C_6)$alkoxy, and R is —O—C(O)—NH—$R^{30}$, especially compounds wherein $R^a$ is —OH, $R^b$ is H and $R^{30}$ is 2-fluorophenyl; 3) R, $R^a$ and $R^b$ are independently —OH or —O—C(O)—$R^{30}$ and $R^{30}$ is $(C_1-C_6)$alkyl, T, or T substituted by one or two halogeno or $(C_1-C_6)$alkyl groups, especially compounds wherein R is —OH and $R^a$ and $R^b$ are —O—C(O)—$R^{30}$ wherein $R^{30}$ is 2-furyl; and 4) R, $R^a$ and $R^b$ are independently —OH or halogeno. Three additional classes of preferred are compounds are those wherein the $C^{1'}$ anomeric oxy is beta, wherein the $C^{2'}$ anomeric oxy is beta, and wherein the R group is alpha.

G and G¹ are preferably selected from:

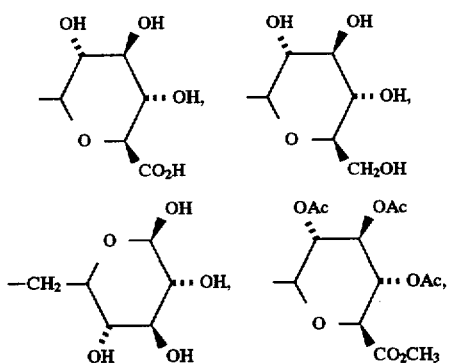

wherein Ac is acetyl and Ph is phenyl. Preferably, $R^{26}$ is H or OH, more preferably H. The —O—G substituent is preferably in the 4-position of the phenyl ring to which it is attached.

This invention also relates to the use of a sugar-substituted 2-azetidinone, especially one of formula I, as a hypocholesterolemic agent in a mammal in need of such treatment.

In another aspect, the invention relates to a pharmaceutical composition comprising a sugar-substituted 2-azetidinone, especially one of formula I, in a pharmaceutically acceptable carrier.

The present invention also relates to a method of reducing hepatic cholesterol ester levels, a method of reducing plasma cholesterol levels, and to a method of treating or preventing atherosclerosis, comprising administering to a mammal in need of such treatment an effective amount of a combination of a sugar-substituted 2-azetidinone of this invention, especially one of formula I, and a cholesterol biosynthesis inhibitor. That is, the present invention relates to the use of a sugar-substituted 2-azetidinone for combined use with a cholesterol biosynthesis inhibitor (and, similarly, use of a cholesterol biosynthesis inhibitor for combined use with a sugar-substituted 2-azetidinone) to treat or prevent atherosclerosis or to reduce plasma cholesterol levels.

In yet another aspect, the invention relates to a pharmaceutical composition comprising an effective amount of a sugar-substituted 2-azetidinone, a cholesterol biosynthesis inhibitor, and a pharmaceutically acceptable carrier. In a final aspect, the invention relates to a kit comprising in one container an effective amount of a sugar-substituted 2-azetidinone in a pharmaceutically acceptable carrier, and in a separate container, an effective amount of a cholesterol biosynthesis inhibitor in a pharmaceutically acceptable carrier.

DETAILED DESCRIPTION

As used herein, the term "alkyl" or "lower alkyl" means straight or branched alkyl chains of 1 to 6 carbon atoms and "alkoxy" similarly refers to alkoxy groups having 1 to 6 carbon atoms.

"Alkenyl" means straight or branched carbon chains having one or more double bonds in the chain, conjugated or unconjugated. Similarly, "alkynyl" means straight or branched carbon chains having one or more triple bonds in the chain. Where an alkyl, alkenyl or alkynyl chain joins two other variables and is therefore bivalent, the terms alkylene, alkenylene and alkynylene are used.

"Cycloalkyl" means a saturated carbon ring of 3 to 6 carbon atoms, while "cycloalkylene" refers to a corresponding bivalent ring, wherein the points of attachment to other groups include all positional isomers.

"Halogeno" refers to fluorine, chlorine, bromine or iodine radicals.

"Aryl" means phenyl, naphthyl, indenyl, tetrahydronaphthyl or indanyl. "Phenylene" means a bivalent phenyl group, including ortho, meta and para-substitution. $R^{24}$-benzyl and $R^{24}$-benzyloxy refer to benzyl and benzyloxy radicals which are substituted on the phenyl ring.

The above statements, wherein, for example, $R^{19}$, $R^{20}$ and $R^{25}$ are said to be independently selected from a group of substituents, means that $R^{19}$, $R^{20}$ and $R^{25}$ are independently selected, but also that where an $R^{19}$, $R^{20}$ or $R^{25}$ variable occurs more than once in a molecule, those occurrences are independently selected (e.g., if $R^{10}$ is —$OR^{19}$ wherein $R^{19}$ is hydrogen, $R^{11}$ can be —$OR^{19}$ wherein $R^{19}$ is lower alkyl). Those skilled in the art will recognize that the size and nature of the substituent(s) will affect the number of substituents which can be present.

Compounds of the invention have at least one asymmetrical carbon atom and therefore all isomers, including diastereomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Cholesterol biosynthesis inhibitors for use in the combination of the present invention include HMG CoA reductase inhibitors such as lovastatin, pravastatin, fluvastatin, simvastatin and Cl-981; HMG CoA synthetase inhibitors, for example L-659,699 ((E,E-11-[3'R-(hydroxy-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride). Preferred HMG CoA reductase inhibitors are lovastatin, pravastatin, fluvastatin and simvastatin.

The cholesterol-lowering 2-azetidinone portions of the compounds of formula I can be prepared by known methods, for example WO 93/02048 describes the preparation of compounds wherein —$R^1$—Q— is alkylene, alkenylene or alkylene interrupted by a hetero atom, phenylene or cycloalkylene; WO 94/17038 describes the preparation of compounds wherein Q is a spirocyclic group; WO 95/08532 describes the preparation of compounds wherein —$R^1$—Q— is a hydroxy-substituted alkylene group; PCT/US95/03196 describes compounds wherein —$R^1$—Q— is a hydroxy-substituted alkylene attached to the $Ar^1$ moiety through an —O— or $S(O)_{0-2}$— group; and U.S. Ser. No. 08/463,619, filed Jun. 5, 1995, describes the preparation of compounds wherein —$R^1$—Q— is a hydroxy-substituted alkylene group attached the the azetidinone ring by a —$S(O)_{0-2}$— group.

Compounds of the present invention are generally prepared by reacting a 4-(hydroxy- or dihydroxy)-phenyl-2-azetidinone with a sugar derivative. For example, an azetidinone of formula II, wherein $R^{26A}$ is H or OH, is reacted with one equivalent of a sugar derivative of formula III:

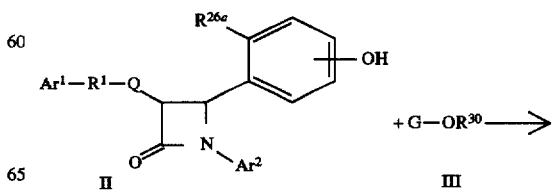

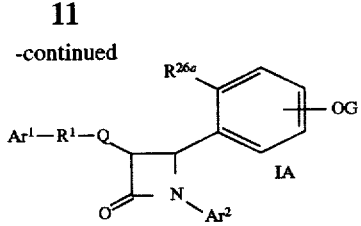

wherein $R^{30}$ is hydrogen or —CNHCCl$_3$ and the remaining variables are as defined above to obtain a compound of formula IA, wherein $R^{26A}$ is H or OH. To prepare a compound of formula IB, wherein $R^{26}$ is OG$^1$, wherein G$^1$ is not H, and G is H, an azetidinone of formula IIA, wherein $R^{26}$ is OH and $R^{27}$ is a suitable hydroxy protecting group, is reacted with a sugar derivative of formula IIIA, wherein $R^{30}$ is as defined above, followed by removal of the $R^{27}$ protecting group:

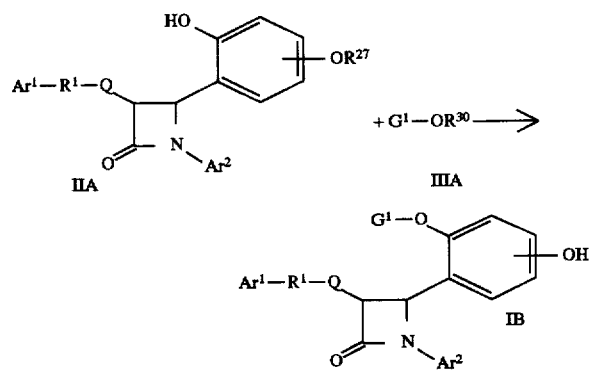

To prepare a compound of formula IC, wherein both G$^1$ and G are the same, but are not H, a dihydroxy compound of formula IIC is reacted with an excess of G—OR$^{30}$:

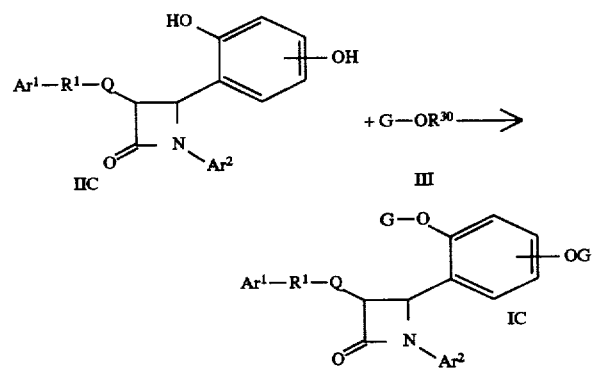

To prepare compounds of formula ID wherein G and G$^1$ are both not H and are not the same sugar derivative, a compound of formula IA wherein $R^{26A}$ is OH can be reacted with a sugar of the formula G$^1$—OR$^{30}$. Alternatively, one of the hydroxy substituents on the 4-position phenyl of a compound of formula IIC is protected prior to reaction with the sugar derivative to be attached to the unprotected hydroxy group, and after reaction with the first sugar derivative, the hydroxy-protecting group is removed and the second sugar derivative is reacted with the previously-protected hydroxy group. For example:

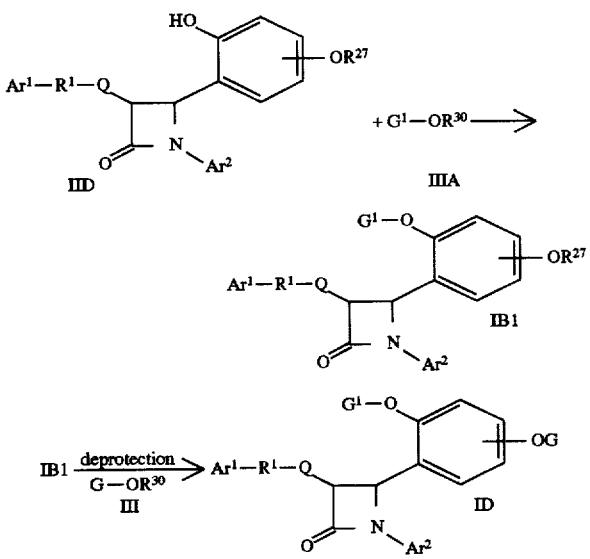

Sugars and the derivatives thereof as defined by G—OR$^{30}$ and G$^1$—OR$^{30}$ are known in the art or are readily prepared by known methods.

Preferably, the reactions described above involve a sugar derivative wherein the non-reactive hydroxy groups are protected by suitable protecting groups as defined above for $R^2$, $R^3$, $R^{3a}$, $R^4$, $R^{4a}$, $R^5$ and $R^7$ other than hydrogen, preferably lower alkyl, acetyl or benzyl, which groups can be removed after the reaction to provide the sugar conjugate. When the 1- and 3-position side chains of the 2-azetidinone include substituent groups which are reactive under the conditions used, said reactive groups are protected by suitable protecting groups prior to reaction with the sugar or the derivative thereof, and the protecting groups are subsequently removed. Depending on the nature of the protecting groups, the protecting groups on the sugar portion and on the 1- and 3-position side chains of the azetidinone can be removed sequentially or simultaneously.

For example, compounds of formula I wherein Ar$^1$—R$^1$—Q— is Ar$^1$—CH(OH)—(CH$_2$)$_2$—, i.e. compounds of formula Ia and Ib, can be prepared according to the following reaction scheme, wherein an azetidinone of formula IIa is reacted with a sugar derivative of the formula G—OCNHCCl$_3$. The scheme is shown for a compound wherein R$_{26}$ is H and a specific G—OCNHCCl$_3$ group is exemplified, but a similar procedure can be used to prepare compounds wherein $R^{26}$ is —OG$^1$ and for other G—OCNHCCl$_3$ groups:

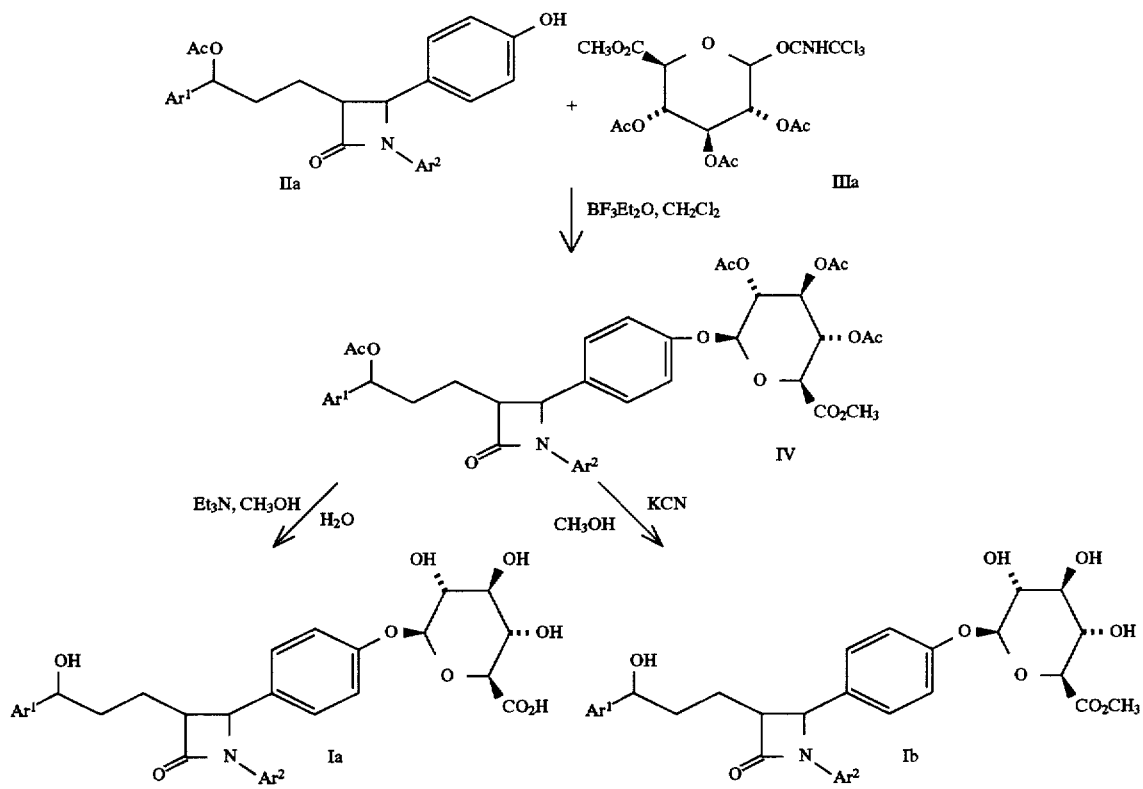

In the first step, the azetidinone of formula IIa is reacted with the sugar derivative of formula IIIa in the presence of a coupling agent such as $BF_3$ etherate in an inert solvent such as $CH_2Cl_2$. The reaction is carried out at temperatures of $-20°$ to $-25°$ C. for a period of about two hours. In the second step, either the sugar-substituted azetidinone of formula IV is treated with a base such as triethylamine in a solvent such as methanol and water to remove the acetyl and alkyl protecting groups to obtain a compound of formula Ia, or the sugar-substituted azetidinone of formula IV is treated with a reagent such as KCN in a solvent such as methanol to remove the acetyl protecting groups but leave the alkyl protecting group to obtain a compound of formula Ib. The compound of formula Ib can be further reduced by a reagent such as LiOH to obtain the compound of formula Ia.

Compounds of formula I wherein $Ar^1$—$R^1$—Q— is $Ar^1$—$(CH_2)_3$—, i.e. compounds of formula Ic, can be prepared according to the following reaction scheme, wherein an azetidinone of formula IIb is reacted with a sugar derivative of the formula G—OH. The scheme is shown for a compound wherein $R^{26}$ is hydrogen and with a specific G—OH group, but a similar procedure can be used to prepare compounds wherein $R^{26}$ is —$OG^1$ and for other G—OH groups:

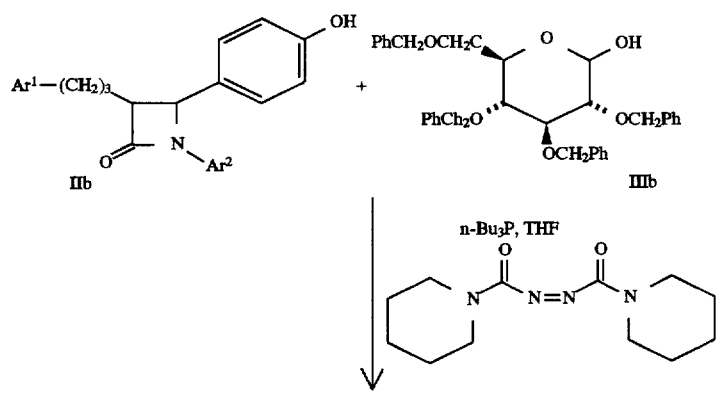

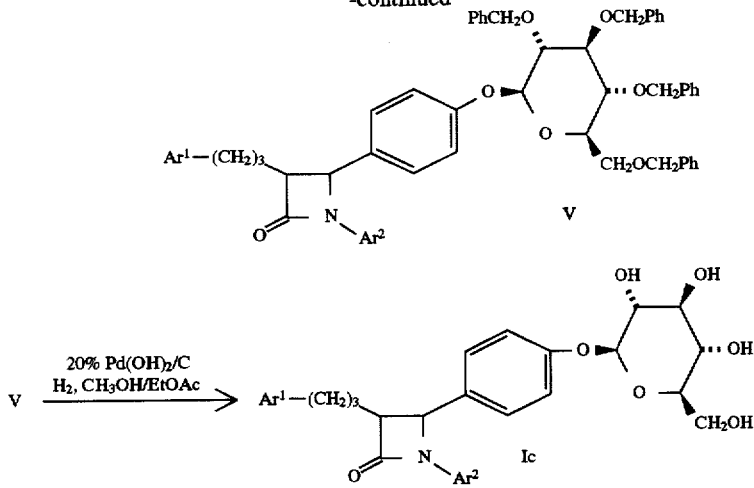

In the first step, the azetidinone of formula IIb is reacted with a sugar derivative of formula IIIb in an inert solvent such as tetrahydrofuran in the presence of n-tributylphosphine and 1,1'-(azodicarbonyl)dipiperidine. The resultant sugar-substituted azetidinone is reduced with a reagent such as Pd(OH)$_2$/C in an alcoholic solvent under H$_2$ gas to remove the benzyl protecting groups to obtain a compound of formula I.

Starting materials of formula IIb are known. Compounds of formula IIa can be prepared from the corresponding (3-hydroxy-3 Ar$^1$-propyl)-2-azetidinone by treatment with acetic anhydride and dimethylaminopyridine (DMAP) in an inert solvent such as CH$_2$Cl$_2$ to obtain the corresponding di-acetyl compound, followed by treatment with guanidine to obtain the 4-hydroxyphenyl compound. Starting materials of formula II wherein Ar$^1$—R$^1$—Q— is as defined above for formula I can be prepared by similar methods or others well known in the art.

Starting materials of formula IIIb are known in the art or prepared by well known methods. Compounds of formula IIIa are prepared by treating the corresponding compound of formula IIIb with trichloroacetonitrile in an inert solvent such as CH$_2$Cl$_2$ in the presence of Cs$_2$CO$_3$.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \>NH | \>NCOalkyl, \>NCObenzyl, \>NCOphenyl |
| | \>NCH$_2$OCH$_2$CH$_2$Si(CH$_3$)$_3$, \>NC(O)OC(CH$_3$)$_3$ |

TABLE 1-continued

| Group to be Protected | Group to be Protected and Protecting Group |
|---|---|
| —NH$_2$ | \>N—benzyl, \>NSi(CH$_3$)$_3$, \>NSi—C(CH$_3$)$_3$ with CH$_3$ groups; succinimido (cyclic N with two C=O) |
| —OH | —OCH$_3$, —OCH$_2$OCH$_3$, —OSi(CH$_3$)$_3$, —OSi—C(CH$_3$)$_3$ with CH$_3$ groups; or —OCH$_2$phenyl |

We have found that the compounds of this invention lower plasma lipid levels and hepatic cholesterol ester levels. Compounds of this invention have been found to inhibit the intestinal absorption of cholesterol and to significantly reduce the formation of liver cholesteryl esters in animal models. Thus, compounds of this invention are hypocholesterolemic agents by virtue of their ability to inhibit the esterification and/or intestinal absorption of cholesterol; they are therefore useful in the treatment and prevention of atherosclerosis in mammals, in particular in humans.

Compared to the 2-azetidinone cholesterol lowering agents which are not sugar-substituted, the compounds of this invention have several pharmacological and physical advantages. The compounds are absorbed at a slower rate, give lower plasma levels and higher intestinal levels. Previous testing indicated the intestine as the likely site of activity of the 2-azetidinone compounds lacking a sugar substituent. See E. J. Sybertz et al, "SCH 48461, a Novel Inhibitor of Cholesterol Absorption," Athersclerosis X, ed. F. P. Woodward et al (Elsevier, 1995), pp. 311–315; and B. G. Salisbury et al, "Hypercholesterolemic Activity of a Novel Inhibitor of Cholesterol Absorption," Athersclerosis, 115 (1995), pp. 45–63. The instantly claimed compounds, which are excreted in the bile, provide efficient delivery of the compound to the desired site while minimizing systemic exposure, thereby decreasing potential toxicity problems.

In addition to the compound aspect, the present invention also relates to a method of lowering plasma cholesterol levels, which method comprises administering to a mammal in need of such treatment a hypocholesterolemic effective amount of a compound of formula I of this invention. The compound is preferably administered in a pharmaceutically acceptable carrier suitable for oral administration.

The present invention also relates to a pharmaceutical composition comprising a compound of formula I of this invention and a pharmaceutically acceptable carrier. The compounds of formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily hypocholesterolemic dose of a compound of formula I is about 0.001 to about 30 mg/kg of body weight per day, preferably about 0.001 to about 1 mg/kg. For an average body weight of 70 kg, the dosage level is therefore from about 0.1 to about 100 mg of drug per day, given in a single dose or 2–4 divided doses. The exact dose, however, is determined by the attending clinician and is dependent on the potency of the compound administered, the age, weight, condition and response of the patient.

For the combinations of this invention wherein the substituted azetidinone is administered in combination with a cholesterol biosynthesis inhibitor, the typical daily dose of the cholesterol biosynthesis inhibitor is 0.1 to 80 mg/kg of mammalian weight per day administered in single or divided dosages, usually once or twice a day: for example, for HMG CoA reductase inhibitors, about 10 to about 40 mg per dose is given 1 to 2 times a day, giving a total daily dose of about 10 to 80 mg per day, and for the other cholesterol biosynthesis inhibitors, about 1 to 1000 mg per dose is given 1 to 2 times a day, giving a total daily dose of about 1 mg to about 2 g per day. The exact dose of any component of the combination to be administered is determined by the attending clinician and is dependent on the potency of the compound administered, the age, weight, condition and response of the patient.

Where the components of a combination are administered separately, the number of doses of each component given per day may not necessarily be the same, e.g. where one component may have a greater duration of activity, and will therefore need to be administered less frequently.

Since the present invention relates to the reduction of plasma cholesterol levels by treatment with a combination of active ingredients wherein said active ingredients may be administered separately, the invention also relates to combining separate pharmaceutical compositions in kit form. That is, a kit is contemplated wherein two separate units are combined: a cholesterol biosynthesis inhibitor pharmaceutical composition and a sugar-substituted 2-azetidinone absorption inhibitor pharmaceutical composition. The kit will preferably include directions for the administration of the separate components. The kit form is particularly advantageous when the separate components must be administered in different dosage forms (e.g. oral and parenteral) or are administered at different dosage intervals.

Following are examples of preparing compounds of formula 1. The stereochemistry listed is relative stereochemistry unless otherwise noted. The terms cis and trans refer to the relative orientations at the β-lactam 3- and 4-positions.

Preparation A 1-(4-Fluorophenyl)-3(R)-[3(S)-acetyloxy-3-(4-fluorophenyl)-propyl)]-4(S)-(4-hydroxyoxyphenyl)-2-azetidinone Step 1: 1-(4-Fluorophenyl-3(R)-[3(S)-acetyloxy-3-(4-fluorophenyl)propyl)]-4(S)-(4-acetyloxyphenyl)-2-azetidinone Add acetic anhydride (1.03 mL, 10.96 mmol) to a room temperature solution of 1-(4-fluorophenyl-3(R)-[3(S)-hydroxy-3-(4-fluorophenyl)propyl)]- 4(S)-(4-hydroxyphenyl)-2-azetidinone (2.04 g, 4.98 mmol) and dimethylaminopyridine (DMAP) (1.46 g, 11.96 mmol) in tetrahydrofuran (THF) (15 mL). After TLC (5% $CH_3OH$/toluene) indicates consumption of starting material (10 min), dilute the mixture with ether ($Et_2O$), wash with 1M HCl and brine, dry over anhydrous $Na_2SO_4$, concentrate to a clear foam 2.47 g (100%) and use without further purification. NMR (400 MHz, $CDCl_3$): 7.33(2H, d, J=8.6 Hz), 7.27(2H, m), 7.21(2H, m), 7.11(2H, d, J=8.5 Hz), 7.02(2H, t, J=8.6 Hz), 6.94(2H, d, J=8.5 Hz), 5.70(1H, t, J=7Hz), 4.60(1H, d, J=2.4 Hz), 3.06(1H, dt, J=7.9, 2.4 Hz), 2.31(3H, s), 2.06(3H, s), 2.03(1H, m), 1.86(2H, M). HRMS (FAB): calcd. for M+H: $C_{28}H_{25}NO_5F_2$, 493.1701; found 493.1695.

Step 2: Add sodium ethoxide (0.338 g, 4.97 mmol) to a room temperature solution of guanadine hydrochloride (0.499 g, 5.22 mmol) in $CH_3OH$ (15 mL). After 10 min, slowly add the resulting solution by pipette to a solution of the product of Step 1 (2.45 g, 4.97 mmol) in $CH_3OH$ (15 mL). Monitor the reaction by TLC (15% EtOAc/toluene), and upon consumption of starting material (~1 h), concentrate the mixture at room temperature in vacuo. Redissolve the resulting residue in ethyl acetate (EtOAc) and concentrate onto enough silica such that a free flowing powder is obtained. Load the resulting powder onto a chromatography column packed with 15% EtOAc/toluene. Elute with the same solvent to obtain 1.31 g (95%) of the title compound as a glass. HRMS (FAB): calcd. for M+H: $C_{26}H_{24}NO_4F_2$, 452.1673; found 452.1661.

Preparation A2

Trans-(3R,4S)-1-(4-(benzoyl)phenyl)-3-(3-phenyl)propyl]-4-(4-hydroxy)phenyl-2-azetidinone Step 1: Reflux a mixture of 4-nitrobenzophenone (20.94 g, 92.2 mmol), ethylene glycol (25.6 mL, 461 mmol), p-toluenesulfonic acid (0.87 g, 4.61 mmol) and toluene (125 mL) overnight with azeotropic removal of water via a Dean-Stark trap. Cool the mixture to room temperature, dilute with $Et_2O$, wash with 1N NaOH, water and brine, dry over anhydrous $Na_2SO_4$ and concentrate to obtain 24.81 g (99%) of a white solid. NMR (400 MHz, $CDCl_3$): 8.18(2H, d, J=9.0 Hz), 7.12(2H, d, J=9.0 Hz), 7.50(2H, d, J=8.0 Hz), 7.34(3H, m), 4.09(4H, m).

Step 2: Dissolve the product of step 1 (24.8 g, 92 mmol) in EtOAc (75 mL), dilute with ethanol (75 mL) and purge with $N_2$. Wash Raney nickel (~40 g) three times with ethanol and transfer to the reaction flask. Hydrogenate the resulting mixture on a Parr shaker at 60 psi until TLC (30% EtOAc/hexanes) indicates consumption of starting material (<2 h). Filter the mixture through celite under a blanket of $N_2$. Wash the filter cake with 50% EtOAc/ethanol and concentrate the filtrate to give 21.6 g (97%) of a solid. NMR (400 MHz, CDCl$_3$): 7.50(2H, d, J=8.0 Hz), 7.30(5H, m), 6.66(2H, d, J=8.6 Hz), 4.03(4H, m).

Step 3: Dissolve the product of step 2 (8.49 g, 35.2 mmol) and 4-(benzyloxy)benzaldehyde (7.47 g, 35.2 mmol) in hot isopropanol (150 ml). Heat the mixture to reflux and allow the isopropanol to escape until a volume of 75 mL is obtained. Dilute the resulting solution with hexanes (200 mL) and allow to stand overnight. Collect the resultant crystals, wash with hexanes and dry under vacuum to give 14.4 g (95%) of white crystals. NMR (400 MHz, CDCl$_3$): 8.36(1H, s), 7.54(4H, m), 7.37(8H, m), 7.08(2H, m), 5.15 (2H, s), 4.08(4H, s). MS(Cl) 436(M+H, 78), 358(39), 149 (100).

Step 4: Add 5-phenylvaleryl chloride (10.7 mL, 53.1 mmol) to a refluxing solution of the product of step 3 (15.4 g, 35.4 mmol) and n-tributylamine (25.3 mL, 106.3 mmol) in toluene (350 mL) and reflux overnight. Cool the mixture to room temperature, quench with 1M HCl, dilute with EtOAc, wash with 1M HCl, NaHCO$_3$ (sat), water and brine, dry over anhydrous Na$_2$SO$_4$ and concentrate onto enough silica gel such that a free flowing powder results. Load the powder onto a chromatography column prepacked with 20% EtOAc/hexanes and elute with the same solvent to obtain 14 g of a solid. Recrystallize from EtOAc/hexanes to obtain 8.54 g (40%) of white crystals. NMR (400 MHz, CDCl$_3$): 7.30 (21H, m), 6.94(2H, d, J=8.6 Hz), 5.03(2H, s), 4.54(1H, d, J=2.4 Hz 4.01(4H, s), 3.07(1H, s), 2.63(2H, t, J=7.0 Hz), 1.92(1H, m), 1.81(3H, m).

Step 5: Add 6N HCl (30 mL) to a solution of the product of step 4 (4.4 g, 7.4 mmol) in THF (120 mL). After 7 h, dilute with EtOAc, wash with NaHCO$_3$ (sat) and brine, dry over anhydrous Na$_2$SO$_4$ and concentrate to give 4.11 g (100%) of a white glass. NMR (400 MHz, CDCl$_3$): 7.72(4H, m), 7.55(1H, m), 7.40(8H, m), 7.27(3H, m), 7.18(3H, m), 6.98 (2H, d, J=8.8 Hz), 5.05(2H, s), 4.65(1H, d, J=2.44 Hz), 3.16(1H, m), 2.65(2H, t, 7.6 Hz), 1.98(1H, m), 1.85(3H, m). HRMS(FAB) calcd for M+H, C$_{38}$H$_{34}$NO$_3$: 552.2539, found 552.2541.

Step 6: Add boron trichloride-dimethylsulfide (14 mL, 28.3 mmol, 2M in CH$_2$Cl$_2$) to a room temperature solution of the product of step 5 (1.56 g, 2.83 mmol) in CH$_2$Cl$_2$ (30 mL). When TLC (20% EtOAc/hexane) indicates consumption of starting material, quench the reaction by the addition of NaHCO$_3$ (sat). Dilute the resulting mixture with EtOAc, wash with NaHCO$_3$ (sat) and brine, dry over anhydrous Na$_2$SO$_4$ and concentrate onto enough silica gel such that a free flowing powder results. Load the powder onto a chromatography column prepacked with 33% EtOAc/hexanes and elute with the same solvent to obtain 1.02 g (78%) of a white glass. NMR (400 MHz, CDCl$_3$): 7.73(4H, m), 7.56 (1H, t, 7.6 Hz), 7.45(2H, t, J=7.6 Hz), 7.34(2H, d, J=8.6 Hz), 7.28(3H, m), 7.2(2H, m), 7.16(2H, d, J=7.3 Hz), 6.85(2H, d, J=8.3 Hz), 4.65(1H, d, J=2.4 Hz), 3.15(1H, m), 2.65(2H, t, J=7.6 Hz), 1.98(1H, m), 1.85(3H, m).

Step 7: Add acetic anhydride (0.43 mL, 4.51 mmol) to a room temperature solution of the product of step 6 (1.61 g, 3.75 mmol) and N,N-dimethylaminiopyridine (0.69 g, 5.64 mmol) in CH$_2$Cl$_2$ (20 mL). When TLC (30% EtOAc/hexanes) indicates consumption of starting material, dilute with EtOAc, wash with 1M HCl, water and brine, dry over anhydrous Na$_2$SO$_4$ and concentrate onto enough silica gel such that a free flowing powder results. Load the powder onto a chromatography column prepacked with 30% EtOAc/hexanes and elute with the same solvent to obtain 1.64 g (78%) of a white glass. Chiral preparative HPLC (Chiracel OD column, 20% EtOH/hexanes, 65 mL/min) provided 0.55 g of enantiomer A and 0.93 g of enantiomer B. NMR (400 MHz, CDCl$_3$): 7.73(4H, m), 7.56(1H, t, J=7.2 Hz), 7.46(2H, t, J=7.7 Hz), 7.32(6H, m), 7.19(3H, m), 7.12(2H, d, J=8.4 Hz), 4.70(1H, d, J=2.44 Hz), 3.17(1H, m), 2.67(2H, t, J=7.6 Hz), 2.31 (3H, s), 1.97(1H, m), 1.86(3H, m). MS(Cl) 504 (M+H, 100), 224(100). Analytical HPLC (Chiracel OD, 20% EtOH/hexanes, 1.0 mL/min) Enantiomer A, Rt=16.83 min, Enantiomer B, Rt=23.83 min.

Step 8: Dissolve LiOH (0.098 g, 2.35 mmol) in water (2.5 mL) and add to a solution the product of step 7, enantiomer B (0.91 g, 1.8 mmol) in THF (7.5 ml). Stir overnight until TLC(30% EtOAc/hexanes) indicates consumption of starting materials. Quench the reaction with 1M HCl, dilute with EtOAc, wash with 1M HCl, water and brine, dry over anhydrous Na$_2$SO$_4$ and concentrate onto enough silica gel such that a free flowing powder results. Load the powder onto a chromatography column prepacked with 30% EtOAc/hexanes and elute with the same solvent to obtain 0.36 g (46%) of a white glass. Analytical HPLC (Chiracel AS, 20% EtOH/hexanes, 0.5 mL/min), Rt=26.81 min. NMR (400 MHz, CDCl$_3$): 7.77(4H, m), 7.56(1H, t, J=7.6 Hz), 7.45(2H, t, J=7.6 Hz), 7.34(2H, d, J=8.6 Hz), 7.28(2H, m), 7.21(3H, m), 7.16(2H, d, J=7 Hz), 6.85(2H, d, J=8.4 Hz), 4.65(1H, d, J=2.4 Hz), 3.15(1H, m), 2.65(2H, t, J=7.4 Hz), 1.98(1H, m), 1.85(3H, m).

Preparation B

Methyl (2,3,4-tri-O-acetyl-D-glucopyransyl)uronate 1-(2,2,2,-trichloroacetimidate)

Add Cs$_2$CO$_3$ (0.49 g, 1.5 mmol) to a room temperature solution of methyl 2,3,4-tri-O-acetyl-D-glucopyranuronate (5.0 g, 15 mmol) and trichloroacetonitrile (3.75 mL, 37.4 mmol) in CH$_2$Cl$_2$ (48 mL), and stir overnight. Filter the resulting brown solution through a cotton plug, washed the filtrate with water, dry over anhydrous Na$_2$SO$_4$ and concentrate. Dissolve the residue in EtOAc and concentrate onto enough silica such that a free flowing powder is obtained. Load the resulting powder onto a chromatography column packed with 30% EtOAc/hexanes. Elute with the same solvent and take only the cleanest fractions to obtain 4.35 g (61%) of the title compound as a glass. NMR (400 MHz, CDCl$_3$): 8.74(1H, s), 6.65(1H, d, J=3.7 Hz), 5.64(1H, t, J=9.8 Hz), 5.27(1H, t, J=9.5 Hz), 5.15(1H, dd, J=3.6, 10 Hz), 4.50(1H, d, J=10.1 Hz), 3.76(3H, s), 2.06(6H, s), 2.02(3H, s).

In a similar manner prepare:

Preparation B2

2,3,6-Tri-O-acetyl-4-O-(2,3,4,6-tetra-O-acetyl-B-D-glucopyranosyl)-α-D-glucopyranosyl 1-(2,2,2,-trichloroacetimidate)

NMR (400 MHz, CDCl$_3$): 8.66(1H, s), 6.49(1H, d, J=3.7 Hz), 5.53(1H, t, J=10 Hz), 5.12(3H, m), 4.94(1H, t, J=8.2 Hz), 4.53(2H, m), 4.40(1H, dd, J=4.2, 12.6 Hz), 4.12(2H, m), 4.05(1H, dd, J=2.1, 12.5 Hz), 3.85(1H, t, J=9.4 Hz), 3.67(1H, m), 2.12(3H, s), 2.10(3H, s), 2.05(3H, s), 2.04(3H, s), 2.02(3H, s), 2.01(3H, s), 2.00(3H, s).

Preparation B3

2,3,4,6-Tetra-O-acetyl-α-D-glucopyranosyl 1-(2,2,2,-Trichloroacetimidate)

NMR (400 MHz, CDCl$_3$): 8.70(1H. s), 6.57(1H, d, J=3.8 Hz), 5.57(1H, t, J=9.8 Hz), 5.19(1H, t, J=9.8 Hz), 5.14(1H, dd, J=3.7, 10.2 Hz), 4.29(1H, dd, J=4, 12.2 Hz), 4.22(1H, m), 4.13(1H, m), 2.09(3H, s), 2.06(3H, s), 2.04(3H, s), 2.03(3H, s). MS(Electrospray): 509(M+NH$_4$).

EXAMPLE 1

1-O-[4-[Trans-(3R,4S)-1-(4-fluorophenyl)-2-oxo-3-[3-[(S)-hydroxy-4-fluorophenyl)propyl]]-4-azetidinyl]phenyl]-Beta-D-glucuronic acid Step 1: 2,3,4-Tri-O-acetyl-1-O-[4-[trans-(3R,4S)-3-[3-[(S)-acetyloxy-3-(4-fluorophenyl)propyl-1-(4-fluorophenyl)-2-oxo-4-azetidinyl]phenyl]-Beta-D-glucopyranuronic acid methyl ester Add boron trifluoride etherate (0.091 mL, 0.74 mmol) to a −25° C. solution of the product of Preparation A (3.33 g, 7.38 mmol) and Preparation B (4.24 g, 8.86 mmol) in CH$_2$Cl$_2$ (74 mL) and maintain the reaction at −20° C. for 2 h. Allow the reaction to warm to 10° C. over 2 h. Quench the mixture with saturated NH$_4$Cl, dilute with EtOAc, wash with saturated NH$_4$Cl, water and brine, dry over anhydrous Na$_2$SO$_4$ and concentrate onto enough silica such that a free flowing powder is obtained. Load the resulting powder onto a chromatography column packed with 40% EtOAc/hexanes. Elute with the same solvent to obtain 5.39 g (95%) as a foam. NMR (400 MHz, CDCl$_3$): 7.26(4H, m), 7.21 (2H, m), 7.01 (4H, m), 6.93(2H, t, J=8.4 Hz), 5.69(1H, t, J=6.7 Hz), 5.34(2H, m), 5.29(1H, m), 5.15(1H, d, J=7.2 Hz), 4.56(1H, d, J=2.1 Hz), 4.17(1H, m), 3.73(3H, s), 3.02(1H, dt, J=7.6, 2.3 Hz), 2.07(14H, m), 1.85(2H, m). HRMS (FAB): calcd. for M+H: C$_{39}$H$_{40}$NO$_{13}$F$_2$, 768.2468; found 768.2460.

Step 2: Dissolve the product of Step 1 (5.08 g, 6.98 mmol) in a mixture of CH$_3$OH (127 mL) and triethylamine (Et$_3$N) (127 mL) at room temperature. Slowly add water (445 mL) via an addition funnel over 10 min in order to maintain a homogeneous solution, then stir the resulting clear yellow solution over night. Quench a small aliquot of the reaction mixture in a vial containing 1M HCl and EtOAc and monitor consumption of the starting material by TLC (5% acetic acid (HOAc)/20% CH$_3$OH/75% CH$_2$Cl$_2$) of the EtOAc layer. Remove the CH$_3$OH and Et$_3$N on a rotary evaporator, acidify the remaining solution with 1M HCl, dilute with EtOAc and extract with EtOAc. Combine the extracts, wash with 1M HCl, water and brine, dry over anhydrous Na$_2$SO$_4$ and concentrate to a white solid 3.82 g (93%). Dissolve the solid in CH$_2$Cl$_2$, and concentrate onto enough silica such that a free flowing powder is obtained. Load the resulting powder onto a chromatography column packed with silica and 15% CH$_3$OH/CH$_2$Cl$_2$. Elute with 5% HOAc/15% CH$_3$OH/80% CH$_2$Cl$_2$. Concentrate the fractions containing the title compound, azeotrope first with toluene (3×) and then CH$_3$OH (5×). Heat the resultant solid to 60° C. under vacuum to remove any residual solvent and obtain the title compound as a white solid 2.6 g (64%). NMR (400 MHz, CD$_3$OD): 7.29(6H, m), 7.09(1H, d, J=8.6 Hz), 6.70(4H, m), 4.96(1H, m), 4.80(1H, d, J=2.0 Hz), 4.59(1H, m), 3.97(1H, d, J=9.6 Hz), 3.59(1H, m), 3.49(2H, m), 3.09(1H, m), 1.86(4H, m). HRMS (FAB): calcd. for M+H: C$_{30}$H$_{30}$NO$_9$F$_2$, 586.1889; found 586.1883.

EXAMPLE 1A

1-O-[4-[Trans-(3R,4S)-1-(4-iodophenyl)-2-oxo-3-[3-[(S)-hydroxy-4-fluorophenyl)propyl]]-4-azetidinyl]phenyl]-Beta-D-glucuronic acid Treat 1-(4-iodophenyl)-3(R)-[3(S)-acetyloxy-3-(4-fluorophenyl)propyl)]-4(S)-(4-hydroxyoxyphenyl)-2-azetidinone and the product of Preparation B according to the procedure described in Example 1 to obtain the title compound. M.p. 135°–137° C.; FAB MS calc'd for C$_{30}$H$_{29}$FINO$_9$ NaCl m/z=751.05, found m/z=751.2.

EXAMPLE 2

1-O-[4-[Trans-(3R,4S)-1-(4-fluorophenyl)-2-oxo-3-[3-[(S)-hydroxy-4-fluorophenyl)propyl]]-4-azetidinyl]phenyl]-3-O-(Beta-D-glucpyranosyl)-Beta-D-glucopyranose Step 1: 2,3,6-Tri-O-acetyl-4-O-(2,3,4,6-tetra-O-acetyl-B-D-glucopyranosyl)-1-O-[4-[trans-(3R,4S)-3-[3(S)-acetyloxy-3-(4-fluorophenyl)propyl-1-(4-fluorophenyl)-2-oxo-4-azetidinyl]phenyl]-Beta-D-glucopyran Using a procedure similar to that described in Example 1, Step 1, combine the product of Preparation A and Preparation B2 to obtain the title compound of Step 1. NMR (400 MHz, CDCl$_3$): 7.23(6H, m), 6.97(6H, m), 5.69(1H, t, 6.6 Hz), 5.26(1H, t, J=9.1 Hz), 5.11(4H, m), 4.95(1H, t, J=8.2 Hz), 4.54(3H, m), 4.39(1H, dd, J=4.3, 12.5 Hz), 4.06(2H, m), 3.87(1H, t, J=9.5 Hz), 3.75(1H, m), 3.68(1H, m), 3.02 (1H, dt, J=2.1, 7.6 Hz), 2.05(26H, m), 1.85(2H, m). HRMS (FAB): calcd. for M+Na: C$_{52}$H$_{57}$NO$_{21}$F$_2$Na, 1092.3289; found 1092.3308.

Step 2: Using a procedure similar to that described in Example 1, Step 2, treat the product of Step 1, above, to obtain the title compound of Example 2. NMR (400 MHz, CD$_3$OD): 7.29(6H, m), 7.10(2H, d, J=8.7 Hz), 7.01(4H, m), 4.96(1H, under CD$_3$OD), 4.81 (1H, d, J=2.2 Hz), 4.60(1H, m), 4.43(1H, d, J=7.9 Hz), 3.88(3H, m), 3.62(4H, m), 3.51 (1H, d, J=8.9 Hz), 3.34(2H, m), 3.24(1H, t, J=8.8 Hz), 3.08(1H, m), 1.88(7H, m). MS (FAB): 756 (M+Na, 70), 734(M+, 100), 716(716, 20).

EXAMPLE 3

1-O-[4-[Trans-(3R,4S)-3-[3(S)-hydroxy-3-(4-fluorophenyl)propyl-1-(4-fluorophenyl)-2-oxo-4-azetidinyl]phenyl]-Beta-D-glucopyranose Step 1: 2,3,4,5-Tetra-O-acetyl-1-O-[4-[trans-(3R,4S)-3-[3 (S)-acetyloxy-3-(4-fluorophenyl)propyl-1-(4-fluorophenyl)-2-oxo-4-azetidinyl]phenyl]-Beta-D-glucopyran Using a procedure similar to that described in Example 1, Step 1, combine the product of Preparation A and Preparation B3 to obtain the title compound of Step 1. NMR (400 MHz, CDCl$_3$): 7.26(4H, m), 7.20 (2H, m), 7.01(4H, m), 6.93(2H, t, J=8.5 Hz), 5.69(1H, t, J=6.5 Hz), 5.29 (2H, m), 5.18(1H, t, J=9.7 Hz), 5.09(1H, d, J=7.3 Hz), 4.56(1H, d, J=2.2 Hz), 4.29(1H, dd, J=5.2, 12.2 Hz), 4.17(1H, dd, J=2.2 Hz, 12.2 Hz), 3.85 (1H, m), 3.03(1H, dt, J=2.1, 7.5 Hz), 2.06(17H, m), 1.85 (2H, m). HRMS (FAB): calcd. for M+Na: C$_{40}$H$_{41}$NO$_{13}$F$_2$Na, 804.2444, found 804.2432.

Step 2: Using a procedure similar to that described in Example 1, Step 2, treat the product of Step 1, above, to obtain the title compound of Example 3. NMR (400 MHz, CD$_3$OD): 7.29(6H, m), 7.11 (2H, d, J=8.8 Hz), 6.98(4H, m), 4.89(1H, under CD$_3$OD), 4.80(1H, d, J=2.2 Hz), 4.60 (1H, m), 3.88(1H, dd, J=2.0, 12.0 Hz), 3.68(1H, dd, J=5.4, 12.0 Hz), 3.41 (3H, m), 3.08(1H, m), 1.86(4H, m). MS (FAB): 572 (M+H, 40), 392(100).

EXAMPLE 4

1-O-[4-[Trans-(3R,4S)-1-(4-fluorophenyl)-2-oxo-3-[3-[(S)-hydroxy-4-fluorophenyl)propyl]]-4-azetidinyl]phenyl]-Beta-D-glucuronic acid methyl ester Add KCN (0.028 g, 0.43 mmol) to a room temperature solution of the product of Example 1, Step 1, (0.312 g, 0.43 mmol) in CH₃OH (5 mL) and stir the mixture overnight. Monitor by TLC (10% CH₃OH/CH₂Cl₂); heat the mixture to 40° C. for 2.5 h. Cool the mixture to room temperature, concentrate onto enough silica such that a free flowing powder is obtained. Load the resulting powder onto a chromatography column packed with silica and 5% CH₃OH/CH₂Cl₂. Elute with 5% CH₃OH/CH₂Cl₂ and collect the purest fractions to obtain 0.116 g of the title compound. NMR (400 MHz, CDCl₃/CD₃OD): 7.16(6H, m), 6.95(4H, m), 6.86(2H, t, J=8.6 Hz), 4.83(1H, d, J=7.6 Hz), 4.56(1H, t, J=6.3 Hz), 4.55(1H, d, J=2.1 Hz), 3.90(1H, d, J=9.8 Hz), 3.73(3H, s), 3.67(1H, t, J=9.1 Hz), 3.51(1H, m), 3.46(1H, t, J=9.2 Hz), 3.30(1H, s), 2.98(1H, m), 1.80(4H, m). HRMS (FAB): calcd. for M+H: $C_{31}H_{32}NO_9F_2$, 600.2045; found 600.2049.

EXAMPLE 5

1-O-[4-[Trans-(3R,4S)-1-(4-methoxyphenyl)-2-oxo-3-(3-phenyl)propyl]-4-azetidinyl]phenyl]-Beta-D-glucuronic acid methyl ester Step 1: 2,3,4-Tri-O-acetyl-1-O-[4-[Trans-(3R,4S)-3-[3-[(S)-acetyloxy-3-(4-fluorophenyl)propyl-1-(4-methoxyphenyl)-2-oxo-4-azetidinyl]phenyl]-Beta-D-glucopyranuronic Acid Methyl Ester Add triphenylphosphine (0.19 g, 0.72 mmol) to a 0° C. solution of 1,1'-(azodicarbonyl)dipiperdine (0.18 g, 0.72 mmol) in THF (3 mL). After 10 min, add (3R,4S)-4-(4-hydroxyphenyl)-1-(4-methoxyphenyl)-3-(3-phenylpropyl)-2-azetidinone (0.2 g, 0.52 mmol), followed by methyl-2,3,4-tri-O-acetyl-D-glucopyranuronate (0.21 g, 0.62 mmol). Allow the mixture to warm to room temperature overnight. Concentrate the mixture onto enough silica such that a free flowing powder is obtained. Load the resulting powder onto a chromatography column packed with silica and 30% EtOAc/hexanes. Elute with 30–50% EtOAc/hexanes to obtain 0.198 g of material which is further purified by silica chromatography eluting with 20% CH₃OH/CH₂Cl₂ to provide 0.074 g of the title compound of Step 1. NMR (400 MHz, CDCl₃): 7.27(4H, m), 7.17(5H, m), 6.98(2H, J=8.5 Hz), 6.77(2H, m), 5.30(3H, m), 5.13(1H, d, J=7.3 Hz), 4.56(1H, d, J=1.9 Hz), 4.17(1H, m), 3.74(3H, s), 3.73(3H, s), 3.04(1H, m), 2.64(2H, t, J=7.6 Hz), 2.05(9H, m), 1.97 (1H, m), 1.82(3H, m). HRMS (FAB): calcd. for M+H: $C_{38}H_{42}NO_{12}$ 704.2707; found 704.2696.

Step 2: Using a procedure similar to that of Example 4, treat the product of Step 1 to obtain the title compound. NMR (400 MHz, CDCl₃): 7.27(4H, m), 7.17(5H, m), 7.04(2H, J=8.6 Hz), 6.75(2H, J=9.1 Hz), 4.90(1H, d, J=7.0 Hz), 4.55(1H, d, J=1.8 Hz), 3.98(1H, d, J=9.7 Hz), 3.88(1H, t, J=8.6 Hz), 3.76(8H, m), 3.03(1H, m), 2.63(2H, t, J=6.7 Hz), 1.95(1H, m), 1.81 (3H, m). HRMS (FAB): calcd. for M+H: $C_{32}H_{36}NO_9$, 578.2390; found 578.2379.

EXAMPLE 6

1-O-[4-[Trans-(3R,4S)-1-(4-(benzoyl)phenyl)-2-oxo-3-(3-phenyl)propyl]-4-azetidinyl]phenyl]-Beta-D-glucuronic acid methyl ester Step 1: 2,3,4-Tri-O-acetyl-1-O-[4-[Trans-(3R,4S)-1-(4-(benzoyl)phenyl)-2-oxo-3-(3-phenyl)propyl]-4-azetidinyl] phenyl]-Beta-D-glucuronic acid methyl ester In a similar manner to Example 5, Step 1, treat (3R,4S)-1-(4-benzoylphenyl)-4-(4-hydroxyphenyl)-3-(3-phenylpropyl)-2-azetidinone and methyl-2,3,4-tri-O-acetyl-D-glucopyranuronate to obtain the title compound of Step 1. NMR (400 MHz, CDCl₃): 7.73(4H, m), 7.57(1H, t, J=7.0 Hz), 7.46(2H, t, J=8.0 Hz), 7.30(6H, m), 7.21(1H, d, J=7.1 Hz), 7.16 (2H, d, J=8.0 Hz), 7.01(2H, d, J=8.5 Hz), 5.31(3H, m), 5.15(1H, d, J=7.3 Hz), 4.67(1H, d, J=2.2 Hz), 4.17(1H, dd, J=2.7, 6.7 Hz), 3.73(3H, s), 3.14 (1H, m), 2.66(2H, t, J=7.4 Hz), 2.06(9H, m), 1.98(1H, m), 1.85(3H, m). HRMS (FAB): calcd. for M+H: $C_{44}H_{44}NO_{12}$, 778.2864; found 778.2849.

Step 2: Using a procedure similar to that of Example 4, treat the product of Step 1 to obtain the title compound. NMR (400 MHz, CDCl₃): 7.72(2H, overlapping d, J=8.6, 7.6 Hz), 7.56(1H, t, J=7.6 Hz), 7.45(2H, t, J=7.7 Hz), 7.30(6H, m), 7.20(1H, d, J=7.0 Hz), 7.16(2H, d, J=7.6 Hz), 7.08(2H, d, J=8.6 Hz), 4.93(1H, d, J=7.0 Hz), 4.67(1H, dd, J=2.1 Hz), 3.99(1H, d, J=9.8 Hz), 3.88(1H, t, J=8.6 Hz), 3.81(3H, s), 3.73(2H, m), 3.14(1H, m), 2.65(2H, t, J=7.6 Hz), 1.98(1H, m), 1.84(3H, m). HRMS (FAB): calcd. for M+H: $C_{38}H_{38}NO_9$, 652.2547; found 652.2528.

EXAMPLE 7

1-O-[4-[Trans-(3R,4S)-1-(4-methoxyphenyl)-2-oxo-3-(3-phenylpropyl)-4-azetidinyl]phenyl]-Beta-D-glucopyranose Step 1: 1-O-[4-[Trans-(3R,4S)-1-(4-methoxyphenyl)-2-oxo-3-(3-phenylpropyl)-4-azetidinyl]phenyl]-2,3,4,6,-tetra-O-(phenylmethyl)-Beta-D-glucopyranose Add n-tributylphosphine (1.45 mL, 5.81 mmol) to a 0° C. solution of 1,1'-(azodicarbonyl)dipiperdine (1.47 g, 5.81 mmol) in THF (30 mL). After 5 min., add (3R,4S)-4-(4-hydroxyphenyl)-1-(4-methoxy-phenyl)-3-( 3-phenylpropyl)-2-azetidinone (1.5 g, 3.87 mmol), followed by 2,3,4,6-tetra-O-benzyl-D-glucopyranose (2.72 g, 5.03 mmol). The reaction becomes very thick, and additional THF (30 mL) is added to facilitate stirring; the mixture is allowed to warm to room temperature overnight. Filter the mixture through celite, wash the filter cake with EtOAc, and concentrate the filtrate onto enough silica such that a free flowing powder is obtained. Load the resulting powder onto a chromatography column packed with silica and 5% EtOAc/toluene. Elute with the same solvent to obtain 3.57 g (~100%) of the title compound of Step 1 as a thick syrup. NMR (400 MHz, CDCl₃): 7.16(19H, m), 7.19(10H, m), 7.04(2H, d, J=8.7 Hz), 6.76(2H, d, J=9.2 Hz), 4.98(3H, m), 4.83(3H, m), 4.55(4H, m), 3.70(9H, m), 3.05(1H, m), 2.65(2H, t, J=7.3 Hz), 1.96 (1H, m), 1.83(3H, m). MS (FAB): 910(M+, 55), 568(40), 478(100), 386(55).

Step 2: Dissolve the product of Step 1 (0.20 g, 0.35 mmol) in CH₃OH (4.5 mL), dilute with EtOAc (4.5 mL) and purge with nitrogen. Add 20% Pd(OH)₂ on carbon (0.35 g), purge the resulting mixture with hydrogen (3×) and then stir under a balloon of hydrogen overnight. Filter the mixture through celite and wash the filter cake with EtOAc followed by CH₃OH. Concentrate the filtrate to a clear foam 0.161 g (83% crude). Purify the foam further by silica chromatography eluting with 5% CH₃OH/EtOAc to obtain 0.127 g (66%) of the the title compound as a white powder. NMR (400 MHz, CD₃OD): 7.18(11H, m), 6.78(2H, d, J=8.9 Hz), 4.88(1H, partially obscured by CD₃OD), 4.72(1H, d, J=1.2 Hz) 3.88(1H, d, J=11.7 Hz), 3.70(4H, m), 3.41(4H, m), 3.03(1H, m), 2.60(2H, t, J=7.0 Hz), 1.79(4H, m). HRMS (FAB): calcd. for M+H: $C_{31}H_{36}NO_8$, 550.2441; found 500.2424.

EXAMPLE 8

1-O-[4-[Trans-(3R,4S)-1-(4-methoxyphenyl)-2-oxo-3-(3-phenylpropyl)-4-azetidinyl]phenyl]-Beta-D-glucuronic acid Step 1: 2,3,4-tri-O-Benzyl-1-O-[4-[trans-(3R,4S)-1-(4-fluorophenyl)-2-oxo-3-[3-[(S)-hydroxy-4-fluorophenyl)propyl]]-4-azetidinyl]phenyl]-Beta-D-glucuronic acid benzyl ester Use (3R,4S)-4-(4-hydroxyphenyl)-1-(4-methoxy-phenyl)-3-(3-phenylpropyl)-2-azetidinone and benzyl 2,3,4-tri-O-benzyl-D-glucopyranuronate in a procedure similar to that described in Example 7, Step 1, to obtain the title compound of Step 1. NMR (400 MHz, CDCl$_3$): 7.22(29H, m), 7.01(2H, d, J=8.7 Hz), 6.77(2H, d, J=9.1 Hz), 5.15(2H, app. d, J=3.8 Hz), 5.01 (1H, d, J=7.2 Hz), 4.97(1H, d, J=11 Hz), 4.90(1H, d, J=11 Hz), 4.80(2H, d, J=11 Hz), 4.74(1H, d, J=10.7 Hz), 4.56(1H, d, J=2.2 Hz), 4.50(1H, d, J=10.7 Hz), 4.04(1H, d, J=9.6 Hz), 3.93(1H, t, J=8.6 Hz), 3.73(5H, m), 3.05(1H, m), 2.65(2H, t, J=7.6 Hz), 1.96(1H, m), 1.83(3H, m). HRMS (FAB): calcd. for M+H: C$_{59}$H$_{58}$NO$_9$ 924.4112; found 924.4119.

Step 2: Using a procedure similar to Example 7, Step 2, treat the product of Step 1 to obtain the title compound of Example 8. NMR (400 MHz, CD$_3$OD): 7.31(2H, d, J=8.9 Hz), 7.21(7H, m), 7.09(2H, d, J=8.7 Hz), 7.81(2H, d, J=8.9 Hz), 4.97(1H, dd, J=1.9, 5.5 Hz), 4.76(1H, d, J=2.0 Hz), 3.97(1H, d, J=9.7 Hz), 3.72(3H, s), 3.60(1H, m), 3.49(2H, m), 3.08(1H, m), 2.64(2H, t, J=7.2 Hz), 1.83(4H, m). HRMS (FAB): calcd. for M+H: C$_{31}$H$_{34}$NO$_9$ 564.2234; found 564.2242.

EXAMPLE 9

1-Methyl-6-O-[4-[trans-(3R,4S)-1-(4-methoxyphenyl)-2-oxo-3-(3-phenylpropyl)-4-azetidinyl]phenyl]-Alpha-D-glucopyranoside Step 1: 1-Methyl-2,3,4-tri-O-Benzyl-6-O-[4-[Trans-(3R,4S)-1-(4-methoxyphenyl)-2-oxo-3-(3-phenylpropyl)-4-azetidinyl]phenyl]-Alpha-D-glucopyranoside Use (3R,4S)-4-(4-hydroxyphenyl)-1-(4-methoxy-phenyl)-3-(3-phenylpropyl)-2-azetidinone and methyl 2,3,4-tri-O-benzyl-D-glucopyranoside in a procedure similar to that described in Example 7, Step 1, to obtain the title compound of Step 1. NMR (400 MHz, CDCl$_3$): 7.26(24H, m), 6.85(2H, d, J=8.6 Hz), 6.74(2H, d, J=9 Hz), 5.01 (1H, d, J=10.7 Hz), 4.86(1H, d, J=11.0 Hz), 4.85(1H, d, J=10.7 Hz), 4.82(1H, d, J=12.1 Hz), 4.69(1H, d, J=12.1 Hz), 4.63(1H, d, J=3.6 Hz), 4.54(1H, d, J=2.3 Hz), 4.51 (1H, d, J=11.0 Hz), 4.09(2H, d, J=2.8 Hz), 4.03(1H, t, J=9.6 Hz), 3.90(1H, d, J=10.1 Hz), 3.72(3H, s), 3.60(1H, dd, J=3.6, 9.6 Hz), 3.38(3H, s), 3.06(1H, m), 2.64(2H, t, J=7.6 Hz), 1.97(1H, m), 1.83(3H, m).

Step 2: Using a procedure similar to Example 7, Step 2, treat the product of Step 1 to obtain the title compound of Example 9. NMR (400 MHz, CDCl$_3$): 7.22(9H, m), 6.94 (2H, d, J=8.6 Hz), 6.76(2H, d, J=8.9 Hz), 4.81 (1H, d, J=3.9 Hz), 4.54(1H, d, J=2.2 Hz), 4.22(2H, m), 3.97(1H, m), 3.71 (5H, m), 3.56(1H, dd, J=3.9, 9.1 Hz), 3.44(3H, s), 3.06(1H, m), 2.64(2H, d, J=7.4 Hz), 1.91(1H, m), 1.82(3H, m). HRMS (FAB): calcd. for M+H: C$_{32}$H$_{38}$NO$_8$ 564.2597, found 564.2578.

EXAMPLE 10

1-O-[4-[Trans-(3R,4S)-1-(4-(benzoyl)phenyl)-2-oxo-3-(3-phenyl)propyl]-4-azetidinyl]phenyl]-Beta-D-glucuronic acid Add LiOH (0.6 mL, 0.6 mmol, 1M) to a room temperature solution of the product of Example 6 (0.064 g, 0.1 mmol) in THF (2 mL). After 50 min., dilute the mixture with EtOAc, quench with HCl (1M), wash with HCl (1M) and brine, dry over anhydrous Na$_2$SO$_4$ and concentrate to a white foam 0.60 g (97%). NMR (400 MHz, CD$_3$OD): 7.67(4H, m), 7.60(1H, m), 7.48(3H, m), 7.36(2H, d, J=8.8 Hz), 7.34(2H, d, J=8.8 Hz), 7.23(2H, m), 7.14(2H, d, J=7.5 Hz), 7.10(2H, d, J=8.7 Hz), 4.97(1H, m), 4.87(1H, d, J=2.2 Hz), 3.97(1H, d, J=9.7 Hz), 3.60(1H, m), 3.49(2H, m), 3.17(1H, m), 2.63(2H, t, J=7.4 Hz), 1.89(1H, m), 1.81(3H, m). HRMS (FAB): calcd. for M+H: C$_{37}$H$_{36}$NO$_9$ 638.2390; found 638.2377.

EXAMPLE 11

1-O-[4-[Trans-(3R,4S)-1-(4-fluorophenyl)-2-oxo-3-[3-[(S)-hydroxy-4-iodophenyl)propyl]]-4-azetidinyl]phenyl]-Beta-D-glucuronic acid Step 1: Condense 1-(4-fluorophenyl)-3(R)-[3(S)-acetyloxy-3-(4-bromophenyl)propyl)]-4(S)-(4-hydroxyphenyl)-2-azetidinone and the product of Preparation B with boron trifluoride etherate according to the procedure described in Example 1. To a solution of the resultant tetraacetate (250 mg, 0.30 mmol) in CH$_3$OH (2 mL) cooled to 0° C., add KCN (10 mg, 0.15 mmol) and stir at room temperature for 2 h, then heat to 45° C. for 4.5 h. Cool the mixture to room temperature and partition between water (20 mL) and EtOAc (30 mL). Wash the EtOAc layer with water and brine, dry (Na$_2$SO$_4$) and concentrate in vacuo. Adsorb the residue (230 mg) onto SiO$_2$ and chromatograph over SiO$_2$ (25 g), eluting with 2% CH$_3$OH in CH$_2$Cl$_2$ progressing to 10% CH$_3$OH in CH$_2$Cl$_2$ to give, after concentration, 84 mg (43%) of the aryl bromide as a solid.

Step 2: To the product of step 1 (25 mg, 0.038 mmol) dissolved in degassed DMF (0.4 mL), add hexabutylditin (220 mg, 38 mmol) and tetrakis triphenylphosphine palladium (4.4 mg, 0.0038 mmol) and heat the mixture to 95° C. under argon for 5 h. Cool the reaction, concentrate in vacuo and adsorb the resulting residue directly onto SiO$_2$. Chromatograph over SiO$_2$ (4 g), eluting with CH$_2$Cl$_2$ progressing to 10% CH$_3$OH in CH$_2$Cl$_2$. Rechromatograph the desired fraction as above and after concentration obtain 7.4 mg (22%) of the desired aryl stannane as a waxy solid.

Step 3: To the product of step 2 (11.8 mg, 0.0135 mmol) dissolved in CH$_3$OH (2 mL) containing pH 5.8 phosphate buffer (0.3 mL), add a 1M solution of NaI in water (14 mL, 0.014 mmol). To this mixture add 68 iodobeads® (~37 mmol) and gently shake the resulting mixture for 1.5 h at room temperature. Filter the iodobeads and wash with EtOH and a small amount of ether. Concentrate the filtrate and partition the residue between EtOAc and 10% aqueous Na$_2$SO$_3$, dry the EtOAc layer (MgSO$_4$) and concentrate in vacuo. Adsorb the residue onto SiO$_2$ and chromatograph over SiO$_2$ (2 g), eluting with CH$_2$Cl$_2$ progressing to 6% CH$_3$OH in CH$_2$Cl$_2$. Concentrate the appropriate fractions to obtain 6.1 mg (64%) of the methyl ester of the title compound as a solid.

Step 4: Stir a solution of the product of step 3 (6.1 mg, 8.6 mmol) in a mixture of water (0.7 mL), triethylamine (0.2 mL) and CH$_3$OH (0.1 mL) at room temperature for 30 min. Concentrate the mixture in vacuo to give 5 mg (83%) of the title compound as a solid. M.p. 157°–159° C., FAB MS calc'd for C$_{30}$H$_{30}$FINO$_9$ m/z=694.1, found m/z=694.1.

The following formulations exemplify some of the dosage forms of this invention. In each, the term "active compound" designates a compound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |

| No. | Ingredient | mg/tablet | mg/tablet |
|---|---|---|---|
| | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Representative formulations comprising a cholesterol biosynthesis inhibitor are well known in the art. It is contemplated that where the two active ingredients are administered as a single composition, the dosage forms disclosed above for substituted azetidinone compounds may readily be modified using the knowledge of one skilled in the art.

The in vivo activity of the compounds of formula I can be determined by the following procedure.

In Vivo Assay of Hypolipidemic Agents Using the Hyperlipidemic Hamster

Hamsters are separated into groups of six and given a controlled cholesterol diet (Purina Chow #5001 containing 0.5% cholesterol) for seven days. Diet consumption is monitored to determine dietary cholesterol exposure in the presence of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by IM injection of ketamine and sacrificed by decapitation. Blood is collected into Vacutainer™ tubes containing EDTA for plasma total cholesterol and triglyceride analysis and the liver excised for free and esterified cholesterol and triglyceride tissue analysis. Data is reported as percent reduction of plasma cholesterol and hepatic cholesterol esters versus control levels.

Using the test procedures described above, the following in vivo data were obtained for representative preferred compounds of formula I. Data is reported as percent change (i.e., percent reduction in plasma cholesterol and in hepatic cholesterol esters) versus control, therefore, negative numbers indicate a positive cholesterol-lowering effect.

| Ex. # | % Reduction in Plasma Cholesterol | % Reduction in Cholesterol Esters | Dose mg/kg |
|---|---|---|---|
| 1 — Step 2 | −58 | −95 | 3 |
| 2 | −52 | −98 | 6 |

For racemic compounds of formula I or active diastereomers or enantiomers of compounds of formula I, compounds administered at dosages of 3 to 10 mg/kg show a range of 0 to −98% reduction in hepatic cholesterol esters, while compounds administered at dosages of 0.01 to 1 mg/kg show a range of −19 to −94% reduction in hepatic cholesterol esters. Compounds preferably show a range of −50 to −98% reduction in hepatic cholesterol esters at a dosage range of 0.01 to 1 mg/kg.

We claim:

1. A compound represented by the structural formula

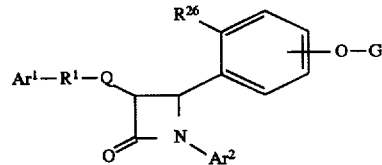

or a pharmaceutically acceptable salt thereof, wherein
$R^{26}$ is H or $OG^1$;
G and $G^1$ are independently selected from the group consisting of

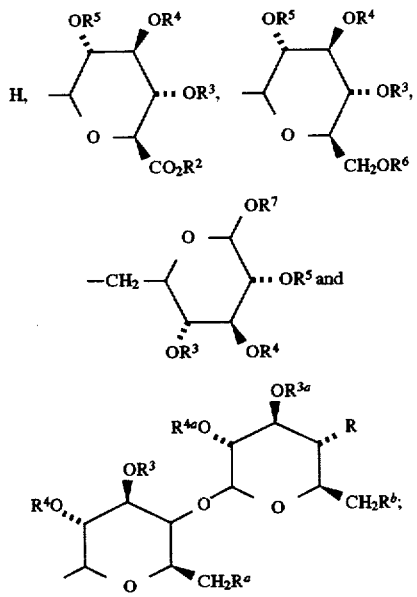

provided that when $R^{26}$ is H or OH, G is not H;

R, $R^a$ and $R^b$ are independently selected from the group consisting of H, —OH, halogen, —$NH_2$, azido, ($C_1$–$C_6$)alkoxy($C_1$–$C_6$)alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, ($C_1$–$C_6$)alkyl, aryl and aryl($C_1$–$C_6$)alkyl;

$R^3$, $R^4$, $R^5$, $R^7$, $R^{3a}$ and $R^{4a}$ are independently selected from the group consisting of H, $(C_1-C_6)$alkyl, aryl $(C_1-C_6)$alkyl, —C(O)$(C_1-C_6)$alkyl and —C(O)aryl;

$R^{30}$ is independently selected from the group consisting of $R^{32}$-substituted T, $R^{32}$-substituted-T-$(C_1-C_6)$alkyl, $R^{32}$-substituted-$(C_2-C_4)$alkenyl, $R^{32}$-substituted-$(C_1-C_6)$alkyl, $R^{32}$-substituted-$(C_3-C_7)$cycloalkyl and $R^{32}$-substituted-$(C_3-C_7)$cycloalkyl$(C_1-C_6)$alkyl;

$R^{31}$ is independently selected from the group consisting of H and $(C_1-C_4)$alkyl;

T is independently selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1–3 substituents independently selected from the group consisting of halogen, $(C_1-C_4)$alkyl, —OH, phenoxy, —CF$_3$, —NO$_2$, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, —N(CH$_3$)$_2$, —C(O)—NH$(C_1-C_4)$alkyl, —C(O)—N$((C_1-C_4)$alkyl)$_2$, —C(O)—$(C_1-C_4)$alkyl, —C(O)—$(C_1-C_4)$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a $(C_1-C_4)$alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is a bond or, with the 3-position ring carbon of the azetidinone, forms the spiro group

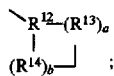

and $R^1$ is selected from the group consisting of

—(CH$_2$)$_q$—, wherein q is 2–6, provided that when Q forms a spiro ring, q can also be zero or 1;

—(CH$_2$)$_e$—E—(CH$_2$)$_r$—, wherein E is —O—, —C(O)—, phenylene, —NR$^{22}$— or —S(O)$_{0-2}$—, e is 0–5 and r is 0–5, provided that the sum of e and r is 1–6;

—(C$_2$-C$_6$)alkenylene-; and

—(CH$_2$)$_f$—V—(CH$_2$)$_g$—, wherein V is C$_3$-C$_6$ cycloalkylene, f is 1–5 and g is 0–5, provided that the sum of f and g is 1–6;

$R^{12}$ is

—CH—, —C(C$_1$-C$_6$ alkyl)—, —CF—, —C(OH)—,

—C(C$_6$H$_4$—R$^{23}$)—, —N—, or —$^+$NO$^-$;

$R^{13}$ and $R^{14}$ are independently selected from the group consisting of —CH$_2$—, —CH(C$_1$-C$_6$ alkyl)-, —C(di-(C$_1$-C$_6$) alkyl), —CH=CH— and —C(C$_1$-C$_6$ alkyl)=CH—; or $R^{12}$ together with an adjacent $R^{13}$, or $R^{12}$ together with an adjacent $R^{14}$, form a —CH=CH— or a —CH=C(C$_1$-C$_6$ alkyl)- group;

a and b are independently 0, 1, 2 or 3, provided both are not zero; provided that when $R^{13}$ is —CH=CH— or —C(C$_1$-C$_6$ alkyl)=CH—, a is 1; provided that when $R^{14}$ is —CH=CH— or —C(C$_1$-C$_6$ alkyl)=CH—, b is 1; provided that when a is 2 or 3, the $R^{13}$'s can be the same or different; and provided that when b is 2 or 3, the $R^{14}$'s can be the same or different;

and when Q is a bond, $R^1$ also can be:

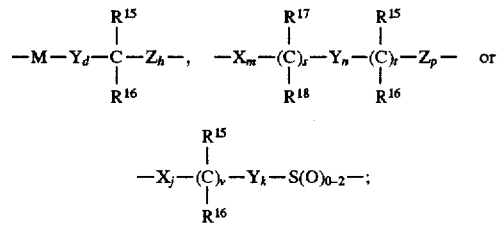

M is —O—, —S—, —S(O)— or —S(O)$_2$—;

X, Y and Z are independently selected from the group consisting of —CH$_2$—, —CH(C$_1$-C$_6$)alkyl- and —C(di-(C$_1$-C$_6$)alkyl);

$R^{10}$ and $R^{11}$ are independently selected from the group consisting of 1–3 substituents independently selected from the group consisting of $(C_1-C_6)$alkyl, —OR$^{19}$, —O(CO) R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^{20}$R$^{25}$, —NR$^{19}$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_2$)$_{1-10}$—COOR$^{19}$, —O(CH$_2$)$_{1-10}$CONR$^{19}$R$^{20}$, —(C$_1$-C$_6$ alkylene)—COOR$^{19}$, —CH=CH—COOR$^{19}$, —CF$_3$, —CN, —NO$_2$ and halogen;

$R^{15}$ and $R^{17}$ are independently selected from the group consisting of —OR$^{19}$, —O(CO)R$^{19}$, —O(CO)OR$^{21}$ and —O(CO)NR$^{19}$R$^{20}$; $R^{16}$ and $R^{18}$ are independently selected from the group consisting of H, $(C_1-C_6)$alkyl and aryl; or $R^{15}$ and $R^{16}$ together are =O, or $R^{17}$ and $R^{18}$ together are =O;

d is 1, 2 or 3;

h is 0, 1, 2, 3 or 4;

s is 0 or 1; t is 0 or 1; m, n and p are independently 0–4; provided that at least one of s and t is 1, and the sum of m, n, p, s and t is 1–6; provided that when p is 0 and t is 1, the sum of m, s and n is 1–5; and provided that when p is 0 and s is 1, the sum of m, t and n is 1–5;

v is 0 or 1;

j and k are independently 1–5, provided that the sum of j, k and v is 1–5;

and when Q is a bond and $R^1$ is

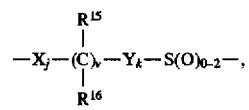

$Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, $(C_1-C_6)$alkyl, aryl and aryl-substituted $(C_1-C_6)$alkyl;

$R^{21}$ is $(C_1-C_6)$alkyl, aryl or $R^{24}$-substituted aryl;

$R^{22}$ is H, $(C_1-C_6)$alkyl, aryl $(C_1-C_6)$alkyl, —C(O)R$^{19}$ or —COOR$^{19}$;

$R^{23}$ and $R^{24}$ are independently 1–3 groups independently selected from the group consisting of H, $(C_1-C_6)$alkyl, $(C_1-C_6)$alkoxy, —COOH, $NO_2$, —$NR^{19}R^{20}$, —OH and halogen; and $R^{25}$ is H, —OH or $(C_1-C_6)$alkoxy.

2. A compound of claim 1 wherein $Ar^1$ is phenyl or $R^{10}$-substituted phenyl and $Ar^2$ is phenyl or $R^{11}$-phenyl.

3. A compound of claim 2 wherein $R^{10}$ is halogen and $R^{11}$ is lower alkoxy or halogen.

4. A compound of claim 1 wherein:

Q is a bond and $R^1$ is lower alkylene;

Q, with the 3-position ring carbon of the azetidinone, forms the group

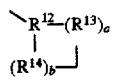

wherein $R^{13}$ and $R^{14}$ are each ethylene and a and b are each 1, and wherein $R^{12}$ is

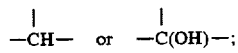

Q is a bond and $R^1$ is —O—$CH_2$—CH(OH)—;
Q is a bond and $R^1$ is —CH(OH)—$(CH_2)_2$—; or
Q is a bond and $R^1$ is —CH(OH)—$CH_2$—$S(O)_{0-2}$—.

5. A compound of claim 1 wherein G and $G^1$ are independently selected from the group consisting of H,

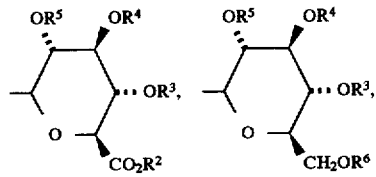

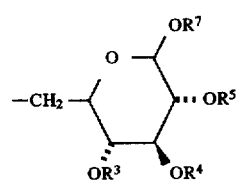

wherein:

$R^2$, $R^3$, $R^4$, $R^5$, $R^6$ and $R^7$ are independently selected from the group consisting of H, $(C_1-C_6)$alkyl, benzyl and acetyl.

6. A compound of claim 1 wherein G and $G^1$ are independently selected from the group consisting of H and

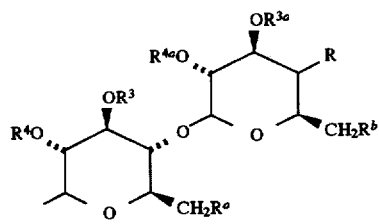

wherein:

$R^3$, $R^{3a}$, $R^4$ and $R^{4a}$ are selected from the group consisting of H, $(C_1-C_6)$alkyl, benzyl and acetyl;

R, $R^a$ and $R^b$ are independently selected from the group consisting of H, —OH, halogen, —$NH_2$, azido, $(C_1-C_6)$alkoxy$(C_1-C_6)$alkoxy and —W—$R^{30}$, wherein W is —O—C(O)— or —O—C(O)—$NR^{31}$—, $R^{31}$ is H and $R^{30}$ is $(C_1-C_6)$alkyl, —C(O)—$(C_1-C_4)$alkoxy-$(C_1-C_6)$alkyl, T, T—$(C_1-C_6)$alkyl, or T or T—$(C_1-C_6)$alkyl wherein T is substituted by one or two halogeno or $(C_1-C_6)$alkyl groups.

7. A compound of claim 6 wherein $R^{30}$ is 2-fluorophenyl, 2,4-difluorophenyl, 2-methylphenyl, 2-thienylmethyl, 2-methoxycarbonyl-ethyl, thiazol-2-yl-methyl, 2-methoxycarbonylbutyl or phenyl.

8. A compound of claim 1 wherein:

$Ar^1$ is phenyl or $R^{10}$-substituted phenyl;

$Ar^2$ is phenyl or $R^{11}$-phenyl;

$R^{10}$ is halogen;

$R^{11}$ is lower alkoxy or halogen;

Q is a bond and $R^1$ is lower alkylene; Q, with the 3-position ring carbon of the azetidinone, forms the group

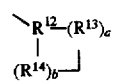

wherein $R^{13}$ and $R^{14}$ are each ethylene and a and b are each 1, and wherein $R^{12}$ is

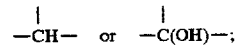

Q is a bond and $R^1$ is —O—$CH_2$—CH(OH)—; Q is a bond and $R^1$ is —CH(OH)—$(CH_2)_2$—; or Q is a bond and $R^1$ is —CH(OH)—$CH_2$—$S(O)_{0-2}$—; and G and $G^1$ are independently selected from the group consisting of

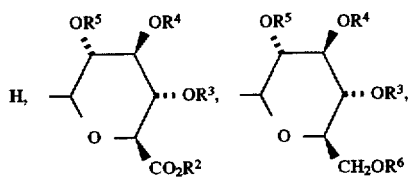

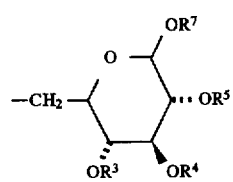

wherein $R^2$, $R^3$, $R^4$, $R^5$, $R^6$ and $R^7$ are independently selected from the group consisting of H, $(C_1-C_6)$alkyl, benzyl and acetyl; or G and $G^1$ are independently selected from the group consisting of H and

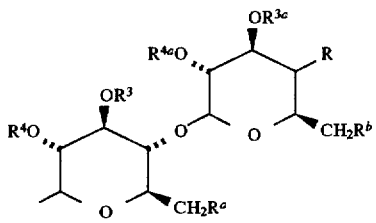

wherein $R^3$, $R^{3a}$, $R^4$ and $R^{4a}$ are selected from the group consisting of H, $(C_1-C_6)$alkyl, benzyl and acetyl; and R, $R^a$ and $R^b$ are independently selected from the group consisting of H, —OH, halogen, —NH$_2$, azido, $(C_1-C_6)$alkoxy$(C_1-C_6)$ alkoxy and —W—$R^{30}$, wherein W is —O—C(O)— or —O— C(O)—NR$^{31}$—, $R^{31}$ is H and $R^{30}$ is $(C_1-C_6)$alkyl, —C(O)—$(C_1-C_4)$alkoxy-$(C_1-C_6)$alkyl, T, T—$(C_1-C_6)$ alkyl, or T or T—$(C_1-C_6)$alkyl wherein T is substituted by one or two halogen or $(C_1-C_6)$alkyl groups.

9. A compound of claim 8 wherein $R^{26}$ is H or OH.

10. A compound of claim 9 wherein G is selected from the group consisting of

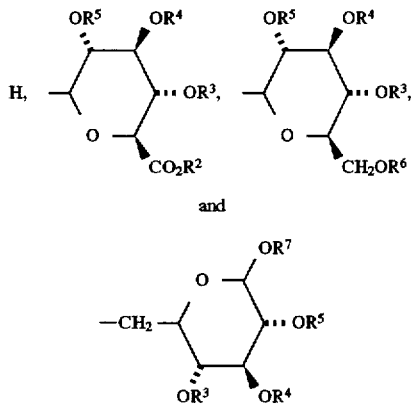

wherein $R^2$, $R^3$, $R^4$, $R^5$, $R^6$ and $R^7$ are independently selected from the group consisting of H, $(C_1-C_6)$alkyl, benzyl and acetyl.

11. A compound of claim 8 wherein G is H and $R^{26}$ is OG$^1$.

12. A compound of claim 8 wherein G is not H and $R^{26}$ is OG$^1$ wherein G$^1$ is not H.

13. A compound of claim 1 selected from the group consisting of 2,3,4-tri-O-acetyl-1-O-[4-[trans-(3R ,4S)-3-[3-[(S)-acetyloxy-3-(4-fluorophenyl)propyl-1-(4-fluorophenyl)-2-oxo-4-azetidinyl]phenyl]-Beta-D-glucopyranuronic acid methyl ester;

1-O-[4-[trans-(3R,4S)-1-(4-fluorophenyl)-2-oxo-3-[3-[(S)-hydroxy-4-fluorophenyl)propyl]]-4-azetidinyl] phenyl]-Beta-D-glucuronic acid;

1-O-[4-[trans-(3R,4S)-1-(4-iodophenyl)-2-oxo-3-[3-[(S)-hydroxy-4-fluorophenyl)propyl]]-4-azetidinyl]phenyl] -Beta-D-glucuronic acid;

2,3,6-tri-O-acetyl-4-O-(2,3,4,6-tetra-O-acetyl-B-D-glucopyranosyl)-1-O-[4-[trans-(3R,4S)-3-[3(S)-acetyloxy-3-(4-fluorophenyl)propyl-1-(4-fluorophenyl)-2-oxo-4-azetidinyl]phenyl]-Beta-D-glucopyran;

1-O-[4-[trans-(3R,4S)-1-(4-fluorophenyl)-2-oxo-3-[3-[(S)-hydroxy-4-fluorophenyl)propyl]]-4-azetidinyl] phenyl]-3-O-(Beta-D-glucpyranosyl)-Beta-D-glucopyranose;

2,3,4,5-tetra-O-acetyl-1-O-[4-[trans-(3R,4S)-3-[3(S)-acetyloxy-3-(4-fluorophenyl)propyl-1-(4-fluorophenyl)-2-oxo-4-azetidinyl]phenyl]-Beta-D-glucopyran;

1-O-[4-[trans-(3R,4S)-3-[3(S)-hydroxy-3-(4-fluorophenyl)propyl-1-(4-fluorophenyl)-2-oxo-4-azetidinyl]phenyl]-Beta-D-glucopyranose;

1-O-[4-[trans-(3R,4S)-1-(4-fluorophenyl)-2-oxo-3-[3-[(S)-hydroxy-4-fluorophenyl)propyl]]-4-azetidinyl] phenyl]-Beta-D-glucuronic acid methyl ester;

1-O-[4-[trans-(3R,4S)-1-(4-methoxyphenyl)-2-oxo-3-(3-phenyl)propyl]-4-azetidinyl]phenyl]-Beta-D-glucuronic acid methyl ester;

1-O-[4-[trans-(3R,4S)-1-(4-(benzoyl)phenyl)-2-oxo-3-(3-phenyl)propyl]-4-azetidinyl]phenyl]-Beta-D-glucuronic acid methyl ester;

1-O-[4-[trans-(3R,4S)-1-(4-methoxyphenyl)-2-oxo-3-(3-phenylpropyl)-4-azetidinyl]phenyl]-Beta-D-glucopyranose;

1-O-[4-[trans-(3R,4S)-1-(4-methoxyphenyl)-2-oxo-3-(3-phenylpropyl)-4-azetidinyl]phenyl]-Beta-D-glucuronic acid;

1-methyl-6-O-[4-[trans-(3R,4S)-1-(4-methoxyphenyl)-2-oxo-3-(3-phenylpropyl)-4-azetidinyl]phenyl]-Alpha-D-glucopyranoside;

1-O-[4-[trans-(3R,4S)-1-(4-(benzoyl)phenyl)-2-oxo-3-(3-phenyl)propyl]-4-azetidinyl]phenyl]-Beta-D-glucuronic acid; and 1-O-[4-[trans-(3R,4S)-1-(4-fluorophenyl)-2-oxo-3-[3-[(S)-hydroxy-4-iodophenyl)propyl]]-4-azetidinyl] phenyl]-Beta-D-glucuronic acid.

14. A method of lowering cholesterol levels in a mammal comprising administering to a mammal in need of such treatment an effective amount of a compound of claim 1.

15. A pharmaceutical composition comprising a cholesterol-lowering effective amount of a compound of claim 1 in a pharmaceutically acceptable carrier.

16. A pharmaceutical composition for the treatment or prevention of atherosclerosis, or for the reduction of cholesterol levels, comprising a compound as defined in claim 1, a cholesterol biosynthesis inhibitor and a pharmaceutically acceptable carrier.

17. A pharmaceutical composition of claim 16 wherein the cholesterol biosynthesis inhibitor is selected from the group consisting of lovastatin, pravastatin, fluvastatin, simvastatin, Cl-981, L-659,699, squalestatin 1 and NB-598.

18. A kit comprising in separate containers in a single package pharmaceutical compositions for use in combination to treat or prevent atherosclerosis or to reduce cholesterol levels which comprises in one container an effective amount of a cholesterol biosynthesis inhibitor in a pharmaceutically acceptable carrier, and in a second container, an effective amount of a compound of claim 1 in a pharmaceutically acceptable carrier.

19. A method of treating or preventing atherosclerosis or reducing cholesterol levels comprising simultaneously or sequentially administering to a mammal in need of such treatment an effective amount of a cholesterol biosynthesis inhibitor and a compound of claim 1.

20. A method as claimed in claim 19, wherein the cholesterol biosynthesis inhibitor is selected from the group consisting of lovastatin, pravastatin, fluvastatin, simvastatin, Cl-981, L-659,699, squalestatin 1 and NB-598.

* * * * *